US010252020B2

(12) United States Patent
Wondka et al.

(10) Patent No.: US 10,252,020 B2
(45) Date of Patent: Apr. 9, 2019

(54) VENTILATOR WITH BIOFEEDBACK MONITORING AND CONTROL FOR IMPROVING PATIENT ACTIVITY AND HEALTH

(75) Inventors: Anthony D. Wondka, Thousand Oaks, CA (US); Angela King, Spencerville, IN (US); Joseph Cipollone, San Ramon, CA (US)

(73) Assignee: Breathe Technologies, Inc., Irvine, CA (US)

(*) Notice: Subject to any disclaimer, the term of this patent is extended or adjusted under 35 U.S.C. 154(b) by 1220 days.

(21) Appl. No.: 12/572,033

(22) Filed: Oct. 1, 2009

(65) Prior Publication Data

US 2010/0083968 A1    Apr. 8, 2010

Related U.S. Application Data

(60) Provisional application No. 61/101,826, filed on Oct. 1, 2008.

(51) Int. Cl.
*A61M 16/12* (2006.01)
*A61M 16/06* (2006.01)
(Continued)

(52) U.S. Cl.
CPC ........ *A61M 16/12* (2013.01); *A61M 16/0677* (2014.02); *A61M 16/125* (2014.02);
(Continued)

(58) Field of Classification Search
CPC .................. A61M 16/00; A61M 2016/0018
(Continued)

(56) References Cited

U.S. PATENT DOCUMENTS 50,641 A    10/1865    Stone
428,592 A    5/1890    Chapman
(Continued)

FOREIGN PATENT DOCUMENTS

DE    19626924    1/1998
DE    29902267 U1    7/1999
(Continued)

OTHER PUBLICATIONS

European Patent Office, Search Report, Application No. 09818525, 4 Pages, dated Mar. 12, 2014.
(Continued)

*Primary Examiner* — LaToya M Louis
(74) *Attorney, Agent, or Firm* — Stetina Brunda Garred and Brucker; Mark B. Garred

(57) ABSTRACT

A respiratory support ventilator apparatus mechanically supports the work of respiration of a patient. The ventilator apparatus is highly portable and optionally wearable so as to promote mobility and physical activity of the patient, and to improve the overall health of the patient. The respiratory support ventilator may monitor a physical activity level and overall health status of the patient, and process this information. The information is used to track efficacy of the ventilation therapy relative to activity level and quality of life, and or to titrate or optimize the ventilation parameters to improve, maintain or optimize the physical activity level and overall health status of the patient.

33 Claims, 13 Drawing Sheets

(51) Int. Cl.
*A61M 16/04* (2006.01)
*A61M 16/00* (2006.01)

(52) U.S. Cl.
CPC ..... *A61M 16/0461* (2013.01); *A61M 16/0463* (2013.01); *A61M 2016/0015* (2013.01); *A61M 2016/0021* (2013.01); *A61M 2205/3569* (2013.01); *A61M 2205/3592* (2013.01); *A61M 2205/502* (2013.01); *A61M 2230/06* (2013.01); *A61M 2230/205* (2013.01); *A61M 2230/42* (2013.01); *A61M 2230/432* (2013.01); *A61M 2230/63* (2013.01); *A61M 2230/65* (2013.01)

(58) Field of Classification Search
USPC ............. 128/204.18, 204.21, 204.23, 204.26
See application file for complete search history.

(56) References Cited

U.S. PATENT DOCUMENTS

| | | |
|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lerner |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |

(56) References Cited

U.S. PATENT DOCUMENTS

| | | | |
|---|---|---|---|
| 4,808,160 A | 2/1989 | Timmons et al. | |
| 4,813,431 A | 3/1989 | Brown | |
| 4,817,897 A | 4/1989 | Kreusel | |
| 4,818,320 A | 4/1989 | Weichselbaum | |
| 4,823,788 A | 4/1989 | Smith et al. | |
| 4,825,859 A | 5/1989 | Lambert | |
| 4,827,922 A | 5/1989 | Champain et al. | |
| 4,832,014 A | 5/1989 | Perkins | |
| 4,838,255 A | 6/1989 | Lambert | |
| 4,841,953 A | 6/1989 | Dodrill | |
| 4,848,333 A | 7/1989 | Waite | |
| 4,850,350 A | 7/1989 | Jackson | |
| 4,865,586 A | 9/1989 | Hedberg | |
| 4,869,718 A | 9/1989 | Brader | |
| 4,899,740 A | 2/1990 | Napolitano | |
| 4,905,688 A | 3/1990 | Vicenzi et al. | |
| 4,915,103 A | 4/1990 | Visveshwara et al. | |
| 4,915,105 A | 4/1990 | Lee | |
| 4,919,128 A | 4/1990 | Kopala et al. | |
| 4,919,132 A | 4/1990 | Miser | |
| 4,938,212 A | 7/1990 | Snook et al. | |
| 4,944,310 A | 7/1990 | Sullivan | |
| 4,967,743 A | 11/1990 | Lambert | |
| 4,971,049 A | 11/1990 | Rotariu et al. | |
| 4,982,735 A | 1/1991 | Yagata et al. | |
| 4,986,269 A | 1/1991 | Hakkinen | |
| 4,989,599 A | 2/1991 | Carter | |
| 4,990,157 A | 2/1991 | Roberts et al. | |
| 5,000,175 A | 3/1991 | Pue | |
| 5,002,050 A | 3/1991 | McGinnis | |
| 5,005,570 A | 4/1991 | Perkins | |
| 5,018,519 A | 5/1991 | Brown | |
| 5,022,394 A | 6/1991 | Chmielinski | |
| 5,024,219 A | 6/1991 | Dietz | |
| 5,025,805 A | 6/1991 | Nutter | |
| 5,038,771 A | 8/1991 | Dietz | |
| 5,042,478 A | 8/1991 | Kopala et al. | |
| 5,046,491 A | 9/1991 | Derrick | |
| 5,046,492 A | 9/1991 | Stackhouse et al. | |
| 5,048,515 A | 9/1991 | Sanso | |
| 5,048,516 A | 9/1991 | Soderberg | |
| 5,052,400 A | 10/1991 | Dietz | |
| 5,054,484 A | 10/1991 | Hebeler, Jr. | |
| 5,058,580 A | 10/1991 | Hazard | |
| 5,074,299 A | 12/1991 | Dietz | |
| 5,076,267 A | 12/1991 | Pasternack | |
| 5,090,408 A | 2/1992 | Spofford et al. | |
| 5,097,827 A | 3/1992 | Izumi | |
| 5,099,836 A | 3/1992 | Rowland et al. | |
| 5,099,837 A | 3/1992 | Russel, Sr. et al. | |
| 5,101,820 A | 4/1992 | Christopher | |
| 5,103,815 A | 4/1992 | Siegel et al. | |
| 5,105,807 A | 4/1992 | Kahn et al. | |
| 5,107,830 A | 4/1992 | Younes | |
| 5,107,831 A | 4/1992 | Halpern et al. | |
| 5,113,857 A | 5/1992 | Dickerman et al. | |
| 5,117,818 A | 6/1992 | Palfy | |
| 5,117,819 A | 6/1992 | Servidio et al. | |
| 5,127,400 A | 7/1992 | DeVries et al. | |
| 5,134,995 A | 8/1992 | Gruenke et al. | |
| 5,134,996 A | 8/1992 | Bell | |
| 5,140,045 A | 8/1992 | Askanazi et al. | |
| 5,148,802 A | 9/1992 | Sanders et al. | |
| 5,161,525 A | 11/1992 | Kimm et al. | |
| 5,165,397 A | 11/1992 | Arp | |
| 5,181,509 A | 1/1993 | Spofford et al. | |
| 5,184,610 A | 2/1993 | Marten et al. | |
| 5,186,167 A | 2/1993 | Kolobow | |
| 5,193,532 A | 3/1993 | Moa et al. | |
| 5,193,533 A | 3/1993 | Body et al. | |
| 5,199,424 A | 4/1993 | Sullivan et al. | |
| 5,211,170 A | 5/1993 | Press | |
| 5,217,008 A | 6/1993 | Lindholm | |
| 5,233,978 A | 8/1993 | Callaway | |
| 5,233,979 A | 8/1993 | Strickland | |
| 5,239,994 A | 8/1993 | Atkins | |
| 5,239,995 A | 8/1993 | Estes et al. | |
| 5,243,972 A | 9/1993 | Huang | |
| 5,245,995 A | 9/1993 | Sullivan et al. | |
| 5,255,675 A | 10/1993 | Kolobow | |
| 5,258,027 A | 11/1993 | Berghaus | |
| 5,269,296 A | 12/1993 | Landis | |
| 5,271,388 A | 12/1993 | Whitwam et al. | |
| 5,271,391 A | 12/1993 | Graves | |
| 5,275,159 A | 1/1994 | Griebel | |
| 5,279,288 A | 1/1994 | Christopher | |
| 5,287,852 A | 2/1994 | Arkinstall | |
| 5,298,189 A | 3/1994 | Kauffman | |
| 5,303,698 A | 4/1994 | Tobia et al. | |
| 5,303,700 A | 4/1994 | Weismann et al. | |
| 5,318,019 A | 6/1994 | Celaya | |
| 5,331,995 A | 7/1994 | Westfall et al. | |
| 5,335,656 A | 8/1994 | Bowe et al. | |
| 5,339,809 A | 8/1994 | Beck, Jr. et al. | |
| 5,349,946 A | 9/1994 | McComb | |
| 5,368,017 A | 11/1994 | Sorenson et al. | |
| 5,370,112 A | 12/1994 | Perkins | |
| 5,373,842 A | 12/1994 | Olsson et al. | |
| 5,375,593 A | 12/1994 | Press | |
| 5,388,575 A | 2/1995 | Taube | |
| 5,394,870 A | 3/1995 | Johansson | |
| 5,398,676 A | 3/1995 | Press et al. | |
| 5,398,682 A | 3/1995 | Lynn | |
| 5,400,778 A | 3/1995 | Jonson et al. | |
| 5,419,314 A | 5/1995 | Christopher | |
| 5,438,979 A | 8/1995 | Johnson, Jr. et al. | |
| 5,438,980 A | 8/1995 | Phillips | |
| 5,443,075 A | 8/1995 | Holscher | |
| 5,460,174 A | 10/1995 | Chang | |
| 5,460,613 A | 10/1995 | Ulrich et al. | |
| 5,474,062 A | 12/1995 | DeVires et al. | |
| 5,477,852 A | 12/1995 | Landis et al. | |
| 5,485,850 A | 1/1996 | Dietz | |
| 5,490,502 A | 2/1996 | Rapoport et al. | |
| 5,503,146 A | 4/1996 | Froehlich et al. | |
| 5,503,497 A | 4/1996 | Dudley et al. | |
| 5,507,282 A | 4/1996 | Younes | |
| 5,509,409 A | 4/1996 | Weatherholt | |
| 5,513,628 A | 5/1996 | Coles et al. | |
| 5,513,631 A | 5/1996 | McWilliams | |
| 5,513,635 A | 5/1996 | Bedi | |
| 5,522,382 A | 6/1996 | Sullivan et al. | |
| 5,526,806 A | 6/1996 | Sansoni | |
| 5,529,060 A | 6/1996 | Salmon et al. | |
| 5,533,506 A | 7/1996 | Wood | |
| 5,535,738 A | 7/1996 | Estes et al. | |
| 5,537,997 A | 7/1996 | Mechlenburg et al. | |
| 5,538,002 A | 7/1996 | Boussignac et al. | |
| 5,542,415 A | 8/1996 | Brody | |
| 5,546,935 A | 8/1996 | Champeau | |
| 5,549,106 A | 8/1996 | Gruenke et al. | |
| 5,551,419 A | 9/1996 | Froehlich et al. | |
| 5,558,086 A | 9/1996 | Smith et al. | |
| 5,564,416 A | 10/1996 | Jones | |
| 5,575,282 A | 11/1996 | Knoch et al. | |
| 5,582,164 A | 12/1996 | Sanders | |
| 5,593,143 A | 1/1997 | Ferrarin | |
| 5,595,174 A | 1/1997 | Gwaltney | |
| 5,598,837 A | 2/1997 | Sirianne, Jr. et al. | |
| 5,598,840 A | 2/1997 | Iund et al. | |
| 5,603,315 A | 2/1997 | Sasso, Jr. | |
| 5,605,148 A | 2/1997 | Jones | |
| 5,626,131 A | 5/1997 | Chua et al. | |
| 5,632,269 A | 5/1997 | Zdrojkowski | |
| 5,636,630 A | 6/1997 | Miller et al. | |
| 5,645,053 A | 7/1997 | Remmers et al. | |
| 5,645,054 A | 7/1997 | Cotner et al. | |
| 5,647,351 A | 7/1997 | Weismann et al. | |
| 5,669,377 A | 9/1997 | Fenn | |
| 5,669,380 A | 9/1997 | Garry et al. | |
| 5,676,132 A | 10/1997 | Tillotson et al. | |
| 5,676,135 A | 10/1997 | McClean | |
| 5,682,878 A | 11/1997 | Ogden | |
| 5,682,881 A | 11/1997 | Winthrop et al. | |

(56) References Cited

U.S. PATENT DOCUMENTS

| | | |
|---|---|---|
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,928,189 A * | 7/1999 | Phillips et al. .............. 604/65 |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 * | 2/2001 | Miller, Jr. .............. 128/204.21 |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |

(56) References Cited

U.S. PATENT DOCUMENTS

| | | |
|---|---|---|
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goer et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |

(56) References Cited

U.S. PATENT DOCUMENTS

| | | |
|---|---|---|
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0096174 A1* | 7/2002 | Hill et al. ............... 128/205.11 |
| 2002/0112730 A1 | 8/2002 | Dutkiewicz |
| 2002/0133378 A1* | 9/2002 | Mault ............... A61B 5/0002 705/3 |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1* | 8/2004 | Schmidt et al. ......... 128/204.23 |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034721 A1* | 2/2005 | Freitag ............... 128/200.24 |
| 2005/0034724 A1 | 2/2005 | O'Dea |

(56) References Cited

U.S. PATENT DOCUMENTS

| | | |
|---|---|---|
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0131288 A1* | 6/2005 | Turner et al. .................. 600/391 |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0235280 A1* | 10/2006 | Vonk ...................... G06F 19/322 600/300 |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1* | 7/2007 | Teller et al. .................. 600/300 |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunarathnam et al. |
| 2008/0092905 A1 | 4/2008 | Gunarathnam et al. |
| 2008/0092906 A1 | 4/2008 | Gunarathnam et al. |
| 2008/0099024 A1 | 5/2008 | Gunarathnam et al. |
| 2008/0099027 A1 | 5/2008 | Gunaratnam et al. |
| 2008/0105264 A1 | 5/2008 | Gunarathnam et al. |
| 2008/0110462 A1 | 5/2008 | Chekal et al. |
| 2008/0121230 A1 | 5/2008 | Cortez et al. |
| 2008/0135044 A1* | 6/2008 | Freitag .................. A61M 16/16 128/200.26 |
| 2008/0142019 A1 | 6/2008 | Lewis et al. |
| 2008/0161653 A1* | 7/2008 | Lin et al. ...................... 600/300 |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |

(56) References Cited

U.S. PATENT DOCUMENTS

| | | |
|---|---|---|
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0241958 A1* | 10/2009 | Baker, Jr. ............... 128/204.23 |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| WO | WO-1992/11054 | 7/1992 |
| WO | WO-1998/01176 | 1/1998 |
| WO | WO-1999/04841 | 2/1999 |
| WO | 9913931 | 3/1999 |
| WO | WO9913931 | 3/1999 |
| WO | WO-2000/064521 | 11/2000 |
| WO | WO-2001/076655 | 10/2001 |
| WO | WO-2002/062413 | 8/2002 |
| WO | WO-2004/009169 | 1/2004 |
| WO | WO-2005/014091 | 2/2005 |
| WO | WO-2005/018524 | 3/2005 |
| WO | WO-2006/138580 | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO2008019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |
| WO | WO-2009/136101 | 11/2009 |
| WO | WO-2009/139647 | 11/2009 |

(56) References Cited

FOREIGN PATENT DOCUMENTS

| WO | WO-2009/149351 | 12/2009 |
|---|---|---|
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO-2010/022363 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO 2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO-2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

European Patent Office, Office Action Examination, Application No. 09818525.9, 4 Pages.
JP Office Action, 2 Pages.
English Traslation JP Office Action, Application No. 2011-530250, 2 Pages.
European Patent Office, Examination, Application No. 09818525.9, 4 Pages.
Examination Report in relation to Application No. 09818525.9; 4 pages.
PCT International Application Published Under the Patent Cooperation Treaty (PCT) in relation to International Publication No. WO 99/13931 dated Mar. 25, 2009; 63 pages.
Supplementary European Search Report in relation to Application No. EP 09818525 dated Feb. 14, 2014; 4 pages.
Canadian Office Action for CA Application No. 2,739,435, dated Jan. 23, 2017.
Austin, Michael A et al. "Effect of High Flow Oxygen on Mortality in Chronic Obstructive Pulmonary Disease Patients in Prehospital Setting: Randomised Controlled Trial." The BMJ 341 (2010): c5462. PMC. Web. Sep. 18, 2017.
Canadian Office Action for CA 2,739, 435; dated Feb. 19, 2018.
Makris and Bouros, "COPD exacerbation: Lost in Translation," BMC Pulonary Medicine, 9:6, pp. 1-3, doi: 10.1186/1471-2466-9-6, Jan. 29, 2009 (Jan. 29, 2009).
In the U.S. Patent and Trademark Office, Supplemental Notice of Allowance dated in re: U.S. Appl. No. 10/771,803, dated Dec. 2, 2008, 2 pages.
In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Aciton in re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.

(56) References Cited

OTHER PUBLICATIONS

In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, Ex Parte Quayle Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-22.
Bauer et al., "ADAM Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.

Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
MacInryre, "Long-Term Oxygen Therapy: Conference Summary," *Resp. Care*, 2000: 45(2), pp. 237-245.
MacIntyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.

(56) References Cited

OTHER PUBLICATIONS

Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the SCOOP(R) System," *Pneumologie*, 1996: 50(10), pp. 700-702. (English Abstract provided.).
Rothfleisch et al., "Facilitation of fiberoptic nasotracheal intubation in a morbidly obese patient by simultaneous use of nasal CPAP," Chest, 1994, 106(1): 287-288.
Sanders et al., "CPAP Via Nasal Mask: A Treatment for Occlusive Sleep Apnea," *Chest*, 1983: 83(1), pp. 144-145.
Sinderby et al., "Neural control of mechanical ventilation in respiratory failure," *Nat. Med.*, 1999: 5(12), pp. 1433-1436.
Somfay et al., "Dose-Response Effect of Oxygen on Hyperinflation and Exercise Endurance in Nonhypoxaemic COPD Patients," *Eur. Resp. J.*, 2001: 18, pp. 77-84.
Sullivan et al., "Reversal of Obstructive Sleep Apnoea by Continuous Positive Airway Pressure Applied Through the Nares," *The Lancet*, 1981: 1(8225), pp. 862-865.
Sullivan, "Home treatment of obstructive sleep apnoea with continuous positive airway pressure applied through a nose-mask," *Bull Eur Physiopathol Respir.*, 1984: 20(1), pp. 49-54.
Tiep et al., "Pulsed nasal and transtracheal oxygen delivery," *Chest*, 1990: 97, pp. 364-368.

Tsuboi et al., "Ventilatory Support During Exercise in Patients With Pulmonary Tuberculosis Sequelae," *Chest*, 1997: 112(4), pp. 1000-1007.
*VHA/DOD Clinical Practice Guideline*, "Management of Chronic Obstructive Pulmonary Disease," Aug. 1999, Ver. 1.1a, Updated Nov. 1999.
Wijkstra et al., "Nocturnal non-invasive positive pressure ventilation for stable chronic obstructive pulmonary disease," *Cochrane Database Syst. Rev.*, 2002, 3: 1-22.
Yaeger et al., "Oxygen Therapy Using Pulse and Continuous Flow With a Transtracheal Catheter and a Nasal Cannula," *Chest*, 1994: 106, pp. 854-860.
Walsh, "McGraw Hill Pocket reference Machinists' and Metalworker' Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report dated Oct. 19, 2007 in co-pending EP 04762494.
International Search Report and Written Opinion for PCT/US04/26800 dated Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 dated Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.

* cited by examiner

VENTILATOR WITH BIOFEEDBACK MONITORING AND CONTROL FOR IMPROVING PATIENT ACTIVITY AND HEALTH

PRIORITY CLAIM

This application claims priority to U.S. Provisional Patent Application No. 61/101,826, filed Oct. 1, 2008, the content of which is incorporated herein by reference in its entirety.

CROSS REFERENCE TO RELATED APPLICATIONS

All publications and patent applications mentioned in this specification are herein incorporated by reference to the same extent as if each individual publication or patent application was specifically and individually indicated to be incorporated by reference.

FIELD OF THE INVENTION

The present invention relates to ventilation therapy, respiratory assist devices and other devices intended to provide ventilatory assistance. More specifically, the application relates to an activity-assist ventilation therapy that uses biofeedback control of ventilation, and includes associativity of ventilation parameters with patient activity and quality of life.

BACKGROUND OF THE INVENTION

For the body to take in oxygen and give off carbon dioxide, two components of the respiratory system must function: (1) the lungs must function as a gas-exchanging organ; and (2) the respiratory pump that functions as a ventilation organ that transports air into the lungs and back out again. The breathing center in the brain, central and peripheral nerves, the osseous thorax, and the breathing musculature as well as free, stable respiratory paths are necessary for a correct functioning of the respiratory pump.

In certain diseases there is a constant overload on or exhaustion of the respiratory pump, which often results in respiratory insufficiency, with symptoms including dyspnea and exhaustion. A non-limiting example of a disease in which there is a constant overload on or exhaustion of the respiratory pump is chronic obstructive pulmonary disease (COPD) or pulmonary emphysema with a distended or flat-standing diaphragm. Flat-standing diaphragms have reduced ability to contract. Also, in patients suffering from pulmonary emphysema, respiratory paths are usually extremely slack and tend to collapse. Either a flat-standing diaphragm and/or slack respiratory paths may cause respiratory insufficiency. As a consequence of a flattened, overextended diaphragm, the patient cannot inhale deeply enough. In addition, the patient cannot exhale sufficiently due to collapsing respiratory paths. This results in an insufficient respiration with an undersupply of oxygen and a rise of carbon dioxide in the blood, i.e., a respiratory insufficiency.

Patients with respiratory insufficiency often require or benefit from supplemental oxygen. However, the supplemental oxygen provided by conventional apparatuses and methods is frequently not adequate to increase ventilation and alleviate symptoms of dyspnea and exhaustion. For example, during periods of light exertion, the patient can become severely dyspneic and exhausted and suffer from elevated $CO_2$ levels, due to the mechanical work associated with breathing which can be eight times more than the normal work required for healthy lungs.

A traditional mechanical ventilator can be used invasively with a tracheal tube or with a non-invasive nasal mask to assist in the work of breathing and alleviate dyspnea; however, conventional ventilators significantly limit upper airway functions, such as talking, eating, and swallowing, and also limit normal life activities such as ambulating and bathing. Hence, mechanical ventilators are rarely used voluntarily, and are predominantly used during acute treatment or for palliative care during late stage lung disease near the end of life.

Recently, new types of ventilation therapy have been described in U.S. Pat. Nos. 7,588,033 and 7,487,778. The new respiratory therapy methods and apparatuses described in these applications provide partial respiratory support in an open transtracheal ventilation system, so the patient can have normal upper airway function such as eating, smelling, drinking, talking, swallowing, and expectorating. Because of their unique delivery systems and ventilation output parameters, these new ventilators are able to be configured in a light weight tote-able or even wearable system to enable the patient to engage in other activities of daily life such as mobility, bathing, and exercise, which are not practical or possible when using conventional ventilators.

Because this new ventilation therapy enables activity and a more normal lifestyle, it now becomes meaningful to include in the ventilator's functionality certain intelligence and interactive features related to activity, health status, and lifestyle. These features would not be useful or even contemplated in a conventional ventilator.

Activity level and exercise tolerance is a key indicator of health status of a person with an illness. Maintaining or increasing the patient's activity level via ventilation therapy is described in U.S. Pat. Nos. 7,588,033 and 7,487,778. As maintaining a certain level of activity is expected to improve overall health status, is it is extremely meaningful to measure and track activity level, along with other related indices of health status, and to provide this information in a manner useful to the care provider and patient.

There is a need for improved patient feedback and monitoring in order to better assess the progress or regression in the health status of the patient and the degree of success of the ventilation therapy in enabling and promoting patient activity and overall health and quality of life.

SUMMARY OF THE INVENTION

Embodiments of the present invention may include a ventilator system including a ventilator, which may include a ventilation gas source, a ventilation gas delivery circuit, and a control unit; a patient interface in communication with the ventilation gas delivery circuit; at least one breath sensor; at least one patient activity sensor; wherein the ventilator is adapted to provide mechanical assistance to respiratory muscles to support work of breathing of a spontaneously breathing patient; wherein the ventilator is adapted to be coupled to a patient for permitting ambulation of a respiratory compromised patient while supporting the work of breathing; and wherein the control unit adjusts ventilation based upon activity level of the patient by processing measurements from the at least one breath sensor and the at least one patient activity sensor.

In certain embodiments, the ventilator may report activity level to a remote device. The patient interface may maintain an open airway system to permit the patient to breathe ambient air freely and spontaneously. The at least one patient activity sensor may be a pedometer to record ambulation of the patient or an actigraphy sensor to record activity level of the patient. The control unit may execute a patient exercise test mode. The control unit may detect respiration from the at least one breath sensor and patient activity measure from the at least one patient activity sensor over a predetermined time and processes the respiration and the patient activity measure to adjust the ventilation. The respiration may be a measure of consecutive breaths over the predetermined time, and ventilation is adjusted after a predetermined number of breaths at a predetermined rate. The at least one breath sensor may measure respiration information selected from the group consisting of: spontaneous breath rate, spontaneous breathing I:E ratio, spontaneous inspiratory and expiratory time, spontaneous depth of breathing, and combinations thereof. The control unit may record trends from the at least one breath sensor and the at least one patient activity sensor. The at least one breath sensor may detect an onset or precursor to a respiratory exacerbation, and the control unit executes a change in ventilator parameters to avoid or alleviate the exacerbation. The control unit may export the onset or precursor to a respiratory exacerbation to an external source. The control unit may include a processor and a memory, and wherein the memory stores measured ventilation parameters regarding activity level of the patient, and wherein after a respiratory exacerbation, the stored respiratory status parameters prior to the respiratory exacerbation are used to program a signature for predicting future respiratory exacerbations. The ventilation system may include a display wherein the display indicates an overall health index, wherein the overall health index comprises at least one patient health status measure, and at least one ventilator parameter measure. The ventilation system may include a patient interface for inputting health status normal values or health status goals, and wherein the patient interface displays patient health status compared to the at least one health status normal values or health status goals.

Embodiments of the present invention may include a method of providing ventilation therapy, the method including providing mechanical assistance with a ventilator to the respiratory muscles to support the work of breathing of a spontaneously breathing patient; supplying ventilation gas to the patient with a patient interface that maintains an open airway system to permit the patient to breathe ambient air freely and spontaneously; providing the ventilation gas with a mobile or wearable apparatus to enable patient mobility and ambulation; recording a patient activity related parameter; measuring and recording a spontaneous breathing pattern of the patient; recording the spontaneous breathing pattern of the patient; and reporting the patient activity related parameter.

Certain embodiments may include recording parameters selected from the group consisting of: general health level, vital signs, respiratory status, quality of life level, physical activity level, and combinations thereof. An exercise or activity test of the patient may be administered through the user interface of the ventilator. The method may include measuring and recording the spontaneous breathing history of the patient, and reporting the spontaneous breathing history of the patient. The measuring may include detecting a precursor to a respiratory exacerbation. The measuring may include adjusting the supplying of ventilation gas based upon the patient activity.

Embodiments of the present invention may include ventilator system including a ventilator, which may include a ventilation gas source, a ventilation gas delivery circuit, and a control unit; a patient interface in communication with the ventilation gas delivery circuit; at least one breath sensor; at least one health status measuring sensor; wherein the ventilator is adapted to provide mechanical assistance to respiratory muscles to support work of breathing of a spontaneously breathing patient; wherein the ventilator is adapted to be coupled to a patient for permitting ambulation of a respiratory compromised patient while supporting the work of breathing; and wherein the control unit adjusts ventilation based upon health status level of the patient by processing measurements from the at least one breath sensor and the at least one health status measuring sensor.

In certain embodiments, the ventilator may report activity level to a remote device. The patient interface may maintain an open airway system to permit the patient to breathe ambient air freely and spontaneously. The at least one patient activity sensor may be a pedometer to record ambulation of the patient or an actigraphy sensor to record activity level of the patient. The control unit may execute a patient exercise test mode. The control unit may detect respiration from the at least one breath sensor and patient activity measure from the at least one patient activity sensor over a predetermined time and processes the respiration and the patient activity measure to adjust the ventilation. The respiration may be a measure of consecutive breaths over the predetermined time, and ventilation is adjusted after a predetermined number of breaths at a predetermined rate. The at least one breath sensor may measure respiration information selected from the group consisting of: spontaneous breath rate, spontaneous breathing I:E ratio, spontaneous inspiratory and expiratory time, spontaneous depth of breathing, and combinations thereof. The control unit may record trends from the at least one breath sensor and the at least one patient activity sensor. The at least one breath sensor may detect an onset or precursor to a respiratory exacerbation, and the control unit executes a change in ventilator parameters to avoid or alleviate the exacerbation. The control unit may export the onset or precursor to a respiratory exacerbation to an external source. The control unit may include a processor and a memory, and wherein the memory stores measured ventilation parameters regarding activity level of the patient, and wherein after a respiratory exacerbation, the stored respiratory status parameters prior to the respiratory exacerbation are used to program a signature for predicting future respiratory exacerbations. The ventilation system may include a display wherein the display indicates an overall health index, wherein the overall health index comprises at least one patient health status measure, and at least one ventilator parameter measure. The ventilation system may include a patient interface for inputting health status normal values or health status goals, and wherein the patient interface displays patient health status compared to the at least one health status normal values or health status goals.

Embodiments of the present invention may include a method of providing ventilation therapy, the method including providing mechanical assistance with a ventilator to the respiratory muscles to support the work of breathing of a spontaneously breathing patient; supplying ventilation gas to the patient with a patient interface that maintains an open airway system to permit the patient to breathe ambient air freely and spontaneously; providing the ventilation gas with a mobile or wearable apparatus to enable patient mobility and ambulation; recording a health status related parameter; measuring and recording a spontaneous breathing pattern of the patient; recording the spontaneous breathing pattern of the patient; and reporting the health status related parameter.

Certain embodiments may include recording parameters selected from the group consisting of: general health level, vital signs, respiratory status, quality of life level, physical activity level, and combinations thereof. An exercise or activity test of the patient may be administered through the user interface of the ventilator. The method may include measuring and recording the spontaneous breathing history of the patient, and reporting the spontaneous breathing history of the patient. The measuring may include detecting a precursor to a respiratory exacerbation. The measuring may include adjusting the supplying of ventilation gas based upon the patient activity.

Embodiments may include a mobility assist device including a portable ventilator with a control unit, the control unit comprising a processor and a memory; a health status measuring device, wherein the health status measuring device measures at least one parameter indicating the current health status of a patient relative to a current activity level or a health goal; and wherein information from the health status measuring device is used to adjust the control unit to adjust the ventilation parameters. The control unit may adjust the ventilation parameters based on information from both the health status measuring device and information from at least one breath sensor.

Embodiments of the present invention may include a ventilator apparatus to provide mechanical assistance to the respiratory muscles to support the work of breathing of a spontaneously breathing patient and configured to be toted or worn by the patient in order to permit ambulation of a respiratory compromised patient while supporting their work of breathing, wherein the apparatus comprises a means to measure the activity or mobility level of the patient and a means to report the activity or mobility level to the user or clinician.

Embodiments of the present invention may include a ventilator apparatus to provide mechanical assistance to the respiratory muscles to support the work of breathing of a spontaneously breathing patient, wherein the apparatus comprises; supplying the ventilation gas to the patient with an interface that maintains an open airway system to permit the patient to breathe ambient air freely and spontaneously; providing the ventilation therapy with a mobile or wearable apparatus to enable patient mobility and ambulation; and further comprising measuring the activity or mobility level of the patient and reporting the activity or mobility information to a user or clinician.

Embodiments of the present invention may include a ventilator apparatus to provide mechanical assistance to the respiratory muscles to support the work of breathing of a spontaneously breathing patient, comprising a pedometer wherein the pedometer records the ambulation of the patient and a processing unit to report the ambulation information to a user.

Embodiments of the present invention may include a ventilator apparatus to provide mechanical assistance to the respiratory muscles to support the work of breathing of a spontaneously breathing patient, comprising an actigraphy sensor wherein the actigraphy sensor records the ambulation of the patient and a processing unit to report the activity level information to a user.

Embodiments of the present invention may include a ventilator apparatus to provide mechanical assistance to the respiratory muscles to support the work of breathing of a spontaneously breathing patient, comprising a exercise test mode wherein the exercise test mode comprises a user interface to administer the test, an information processing means to manage the exercise information, and a reporting means to report the test results to a user or clinician.

Embodiments of the present invention may include a ventilator apparatus to provide mechanical assistance to the respiratory muscles to support the work of breathing of a spontaneously breathing patient, wherein the apparatus comprises; supplying the ventilation gas to the patient with an interface that maintains an open airway system to permit the patient to breathe ambient air freely and spontaneously; providing the ventilation therapy with a mobile or wearable apparatus to enable patient mobility and ambulation; and further administering an exercise test to the patient through a user interface and information processing unit in the ventilator, and reporting the results of the exercise test to the user or clinician.

Embodiments of the present invention may include a ventilator apparatus to provide mechanical assistance to the respiratory muscles to support the work of breathing of a spontaneously breathing patient, comprising an automatic ventilator adjustment mode, wherein the automatic ventilator adjustment mode comprises a sensor to detect a patient activity related parameter such as ambulation or physical movement, and comprising a control system to adjust the ventilator output based on the detection of the patient activity related parameter.

Embodiments of the present invention may include a ventilator apparatus to provide mechanical assistance to the respiratory muscles to support the work of breathing of a spontaneously breathing patient, comprising a spontaneous respiration rate breath sensor adapted to measure the patient's spontaneous breath rate, spontaneous breathing I:E ratio, spontaneous inspiratory and expiratory time, and spontaneous depth of breathing, and further comprising a means to record, trend and report on the patient's spontaneous respiration information.

Embodiments of the present invention may include a ventilator apparatus to provide mechanical assistance to the respiratory muscles to support the work of breathing of a spontaneously breathing patient, comprising a detection means to detect the onset or precursor to a respiratory exacerbation, wherein the detection means comprises breathing signal monitoring sensor and a breathing signal processing unit. The recorded values recorded and stored in memory prior to an exacerbation can be used to create a patient-specific precursor signature, which can then be programmed into the system for future detection of further exacerbation events.

Embodiments of the present invention may include a method of providing ventilation therapy comprising: providing mechanical assistance with a ventilator to the respiratory muscles to support the work of breathing of a spontaneously breathing patient; supplying the ventilation gas to the patient with an interface that maintains an open airway system to permit the patient to breathe ambient air freely and spontaneously; providing the ventilation therapy with a mobile or wearable apparatus to enable patient mobility and ambulation; recording a patient activity related parameter; and reporting to a user or clinician the patient activity related parameter.

Embodiments of the present invention may include a method of providing ventilation therapy comprising: providing mechanical assistance with a ventilator to the respiratory muscles to support the work of breathing of a spontaneously breathing patient; supplying the ventilation gas to the patient with an interface that maintains an open airway system to permit the patient to breathe ambient air freely and spontaneously; providing the ventilation therapy with a mobile or wearable apparatus to enable patient mobility and ambulation; recording a patient well-being or quality of life related parameter; and reporting to a user or clinician the patient well-being or quality of life related parameter.

Embodiments of the present invention may include a method of providing ventilation therapy comprising: providing mechanical assistance with a ventilator to the respiratory muscles to support the work of breathing of a spontaneously breathing patient; supplying the ventilation gas to the patient with an interface that maintains an open airway system to permit the patient to breathe ambient air freely and spontaneously; providing the ventilation therapy with a mobile or wearable apparatus to enable patient mobility and ambulation, and administering an exercise or activity test of the patient through the user interface of the ventilator.

Embodiments of the present invention may include a method of providing ventilation therapy comprising: providing mechanical assistance with a ventilator to the respiratory muscles to support the work of breathing of a spontaneously breathing patient; supplying the ventilation gas to the patient with an interface that maintains an open airway system to permit the patient to breathe ambient air freely and spontaneously; providing the ventilation therapy with a mobile or wearable apparatus to enable patient mobility and ambulation, and measuring and recording the spontaneous breathing pattern and history of the patient, and reporting the spontaneous breathing pattern variables and history of the patient to the user or clinician.

Embodiments of the present invention may include a method of providing ventilation therapy comprising: providing mechanical assistance to the respiratory muscles to support the work of breathing of a spontaneously breathing patient; supplying the ventilation gas to the patient with an interface that maintains an open airway system to permit the patient to breathe ambient air freely and spontaneously; providing the ventilation therapy with a mobile or wearable apparatus to enable patient mobility and ambulation; and further detecting the precursor to a respiratory exacerbation and reporting the precursor to the user or clinician. Ventilation therapy may move a patient towards increased activity, sometimes modifying the ventilation therapy to support increased activity, and, eventually, reducing or eliminating the need for ventilation therapy in those cases where the health status of a patient improves so that they can be active without the ventilation therapy. One component in the decision for the modification, reduction, or elimination of the need for ventilation therapy is patient feedback. Patient feedback useful in this determination may include, for example, information on patient activity, or exertion level in the activity or work performed by the patient. In some situations, for example when treating progressive respiratory diseases in which the activity or health goal may be reduced progression of the disease, the patient feedback is used to continually titrate the settings to the overall health goals selected for the patient. The activity or health goals are selected in advance, and may change over time. The monitoring of the patient may indicate how the patient is doing in comparison to the goal. The ventilation parameters can be continually titrated up or down as needed in order to come as close to meeting the overall health goals as possible.

While the invention is described herein in relation to ventilators, it can also be adapted for use with respiratory assist devices, oxygen therapy devices, and any respiratory therapy apparatus or method that is intended to promote or useful for promoting mobility and activities of daily living.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

Figure 1A:
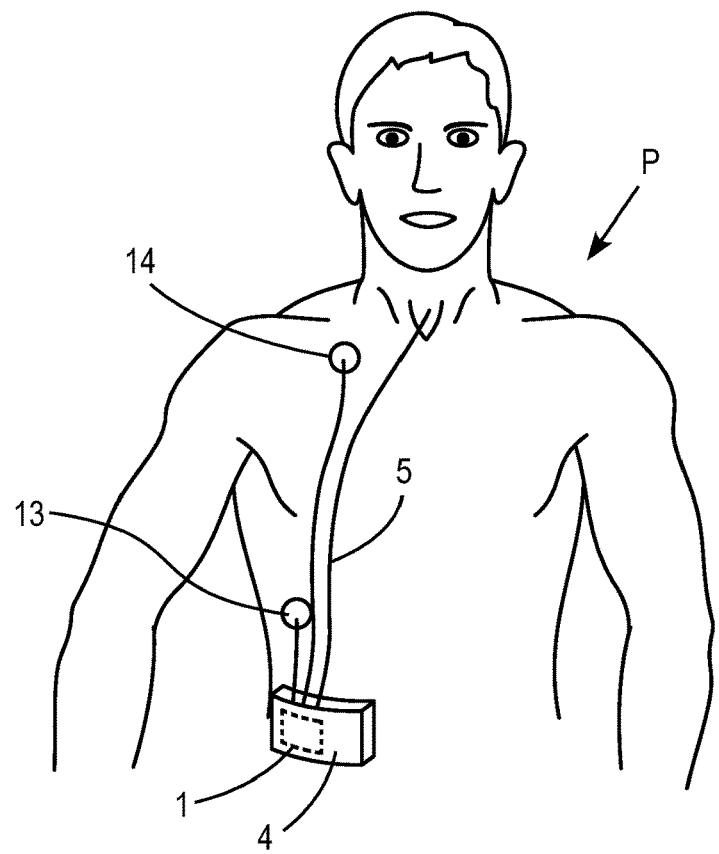
FIG. 1A shows a patient using an exemplary ventilation system according to the invention.

Embodiments of the present invention provide improved systems, methods, and apparatuses for supporting the respiration of a patient using patient input, providing patient feedback, or both. Embodiments of the present invention may provide respiratory support that promotes mobility and activities of daily living, and/or that is more compatible with mobility and activities of daily living as compared to conventional respiratory support systems, methods, and apparatuses. Respiratory support can be accomplished in a variety of ways, including, but not limited to, by providing controlled synchronized ventilation with a directed flow of an oxygen-bearing gas. The oxygen-bearing gas may be, for example, substantially pure oxygen, mixtures of oxygen and nitrogen, mixtures of oxygen and inert gases, ambient air, or various combinations thereof. In addition, the oxygen-bearing gas may include enhancements, such as fragrances, aerosolized drugs, humidification, or heating. Patient input may be provided, for example, via one or more of the wired or wire-less devices discussed below, or by other suitable methods or devices that are known in the art, or which may be discovered, and which the skilled artisan will recognize as suitable when provided with the teachings herein. Patient feedback may be provided, for example, via one or more of the indications, reports, readouts or system data outputs discussed below, or by other suitable methods or devices that are known in the art, or which may be discovered, and which the skilled artisan will recognize as suitable when provided with the teachings herein.

The patient may be ventilated using a ventilation gas delivery circuit and non-invasive open nasal ventilation interface or nasal interface, or a minimally invasive transtracheal interface. The nasal interface preferably does not seal against the patient's nose like in other ventilation interfaces, and rather leaves the nose open for the user to breathe normally and freely from the ambient surroundings. The transtracheal interface connects to the patient's trachea without sealing the airway so the patient can breathe normally and freely through their upper airway. Ventilation gas may be delivered at a speed which entrains ambient air, such that the combination of ventilation gas and entrained air are delivered to the user's airways and lung under power. The interface may optimize the physics and fluid dynamics, in order to maximize its performance, as will be explained in the subsequent detailed descriptions. The ventilation system may also include a ventilator and a gas supply or gas generating means. A spontaneous breathing respiration sensor may also be used to detect, determine and measure the spontaneous breathing pattern and phases of the user, in order to synchronized and titrate the therapy to the needs of the patient and to match the gas delivery comfortably with the patient's breathing. The invention may be used to support the respiration of the patient, including supporting the work of breathing by increasing pressure and volume in the lung, and can be used for maintaining airway patency of the upper airways such as the oropharyngeal airway. When using the invention, the patient breathes normally through their upper airway and through their nose, while receiving mechanical support through the interface. In the case of the nasal interface, the patient can keep their mouth closed during use, to help direct the mechanical support to the lower airways, or can use a bite block or mouth guard or chin band, if necessary. The patient can use the therapy while stationary, while being transported, while mobile and active, or while resting or sleeping. The therapy has homecare, hospital, subacute care, emergency, military, pandemic, and transport applications. An oral interface or endotracheal tube interface is also contemplated as part of the invention, as well as a modular system that is compatible with all interface types mentioned.

A ventilator of the invention can be borne or worn by the patient. The nasal interface may be placed discretely on the user's body, head and face. The transtracheal interface may be discrete and low profile, or in the case the patient has a typical tracheostomy tube, the interface can be minimally invasively connected to the tracheostomy tube. Because the ventilation system contributes to some of the mechanical work required for a person to breathe, the user can be active without suffering from dyspnea, hypoxemia or hypercapnia. The user can benefit from ambulation, activity, and participate in the routine activities of daily living, such as preparing meals, bathing, chores around the house, and leaving the house for outside activities. Further, the user can communicate, eat, drink and swallow, while receiving mechanical ventilation, as opposed to other ventilation interfaces in which the patient's airway is closed with an external mask, or sealed internally with a cuffed airway tube. The ventilation parameters, ventilation timing algorithms, and the effect on the lung are described in subsequent detailed descriptions.

Embodiments of the present invention may include a ventilation therapy device with one or more of a built in or a modular: actigraphy sensor, pedometer, quality of life scale/questionnaire function, and other activity sensors. Embodiments of the present invention may include an exertion, exhaustion, dyspnea or well being scale/questionnaire function or input device. Titration of therapy may be performed based on patient's activity level, automatic adjustment mechanisms, and/or selectable settings of the ventilator system according to the patient's response to therapy. Alternatively or in addition, embodiments of the inventive ventilation therapy device may include indications and/or monitoring of known disease exacerbation prediction. Alternatively or in addition, embodiments of the inventive ventilation therapy device may include the ability to provide report(s) to the health care provider. These may include communication devices that send information from the ventilator to an external source. The report(s) may provide information such as, for example, information regarding a patent's activity levels; information regarding the patient's health status, such as patient vital signs such as oxygen saturation ($SpO_2$) and respiratory rate (RR), the patient's exercise tolerance, respiratory status; and/or information about the operation of the patient's ventilator, such as settings and parameters. Information about a patient's health status, the patient's activity, and the operational parameters of the patient's ventilator can be correlated or associated with each other, such as over time. The report(s) created by systems according to the invention preferably provide the clinician or other health care provider with a more complete picture of the patient's activity level and overall health status as a function of the operation of the ventilator. The additional intelligence provided by the systems according to the invention preferably facilitate the monitoring and tracking of the patient's health and progress, the optimization and/or titration of the ventilation therapy to better meet the needs of the patient, including, but not limited to, changing the parameters of the ventilation therapy to meet changing conditions in the patient's health and/or physical activity level.

The interactive devices and features of systems according to the invention, non-limiting examples of which are described in more detail below, preferably enable the patient or care provider to set activity type goals, administer activity and well being type tests or questionnaires, and report on respiratory status, health status, activity level status, progress and trends. The intelligence and interactive features can preferably also be used to tailor and titrate the ventilation therapeutic level to the needs of the patient. Ventilation therapy may be matched as closely as possible to activity and/or health goals by a control unit.

Figure 1B:
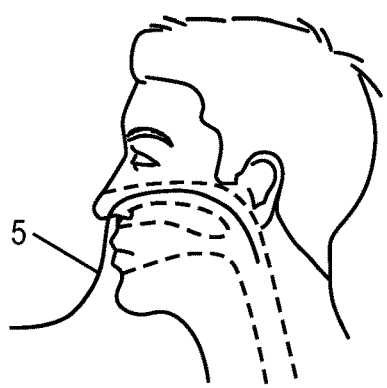
FIGS. 1B and 1C show additional non-limiting examples of different entry routes for a ventilation catheter or gas delivery circuit useful with ventilation system according to the invention.
Figure 1C:
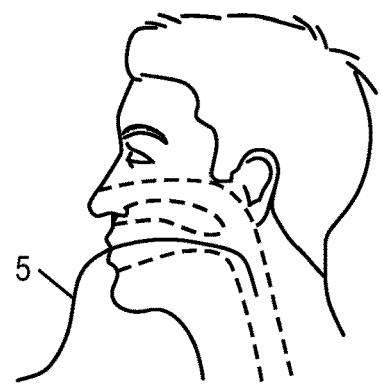

Referring to FIG. 1A, in accordance with one embodiment of the invention, P designates a patient suffering from respiratory insufficiency. Patient P may be, for example, suffering from a breathing disorder, such as pulmonary emphysema, with overloading and exhaustion of the respiratory muscles. As a consequence, the patient P can not take sufficiently sized breaths, and thus too much $CO_2$ is retained in the lungs, which can not be flushed out, and insufficient oxygen is supplied to the tissues. Patient P may additionally suffer, for example, from slack and collapsing respiratory paths, which contribute to the patient's inability to exhale enough carbon-dioxide rich gas, thus, trapping the $CO_2$ rich gas in the lungs. The system of FIG. 1A generally includes the ability to detect the patient's spontaneous respiration via one or more sensors 13, 14 and the ability to perform some of the work of breathing for the respiratory muscles by delivering pressurized gas as a function of patient activity in a manner that results in increased lung pressure in the lung in an open airway system. In addition, a ventilator 4 may provide additional oxygen to the lungs and can be synchronized to augment inspiration, exhalation, or both via a control unit 1. The control unit 1 may include a memory and a processor. The control unit 1 may process measurements taken from one or more types of sensors to adjust ventilation therapy and/or match patient activity and/or health goals. Known patient interfaces may be used with ventilation systems of the present invention. Preferably, as is shown in FIG. 1A, a transtracheal catheter 5 or gas delivery circuit is placed into the patient's airway without sealing the airway, so that the patient's airway is open ambient, thus, permitting and promoting spontaneous breathing through the natural air passages. The ventilation system may promote mobility and normal airway function while still assisting in the work of breathing. The ventilation system may be portable and does not prevent spontaneous breathing. FIGS. 1B and 1C show additional non-limiting examples of patient interfaces. FIG. 1B illustrates a ventilation catheter 5 or gas delivery circuit placed into the patient's trachea via a nasopharyngeal route. Optionally, in FIG. 1B, the ventilation catheter tip can be disposed at the entrance to the nose, or even outside the entrance to the nose. FIG. 1C illustrates a ventilation catheter 5 or gas delivery circuit placed into the patient's trachea via an oropharyngeal route. Embodiments of the present invention may also work with conventional interface devices, such as, but not limited to, a conventional nasal mask.

Figure 2A:
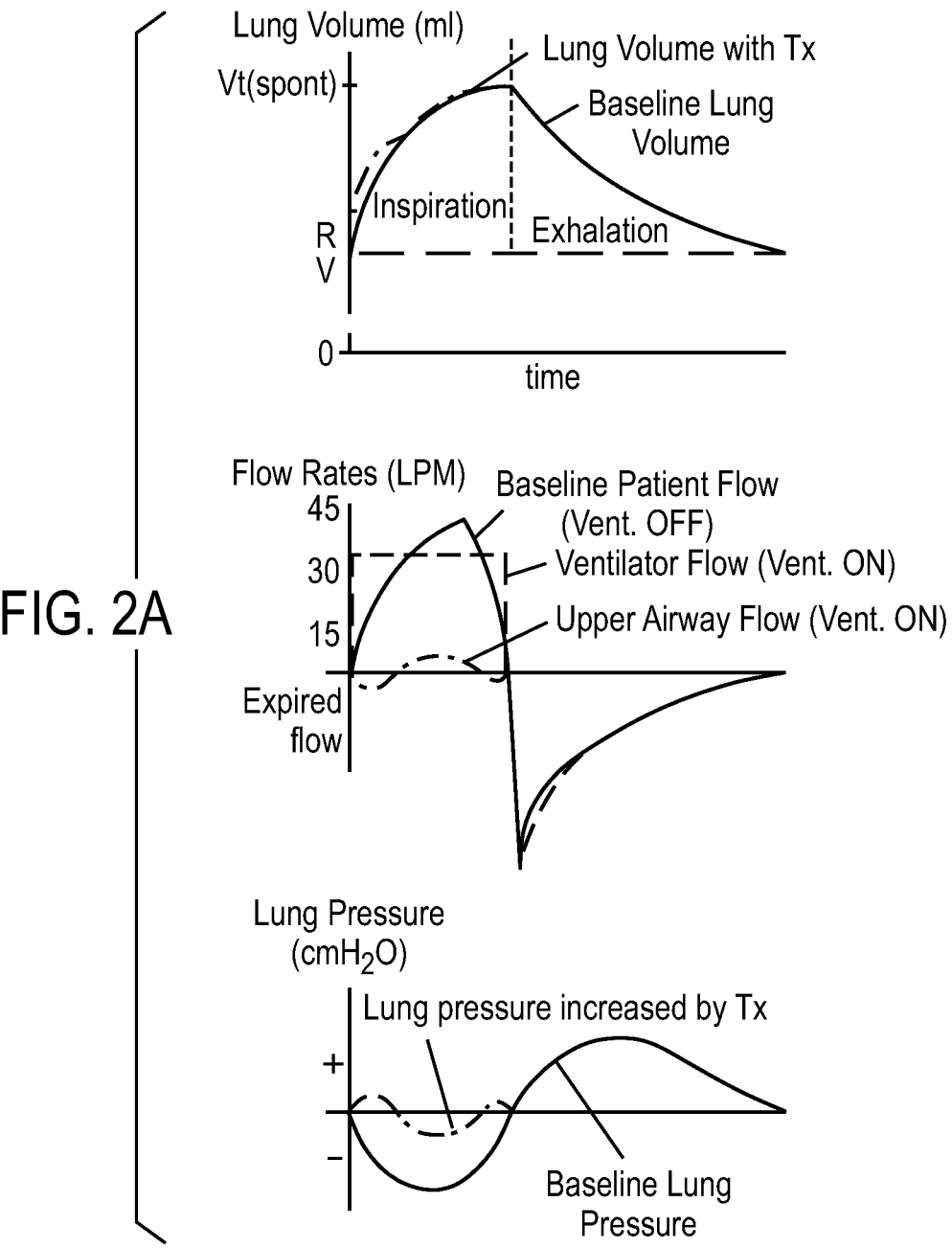
FIGS. 2A, 2B and 2C graphically show non-limiting examples of how a ventilation system according to embodiments of the invention can be efficacious in supporting the work of breathing, mobility and ambulation while using an open airway system.
Figure 2B:
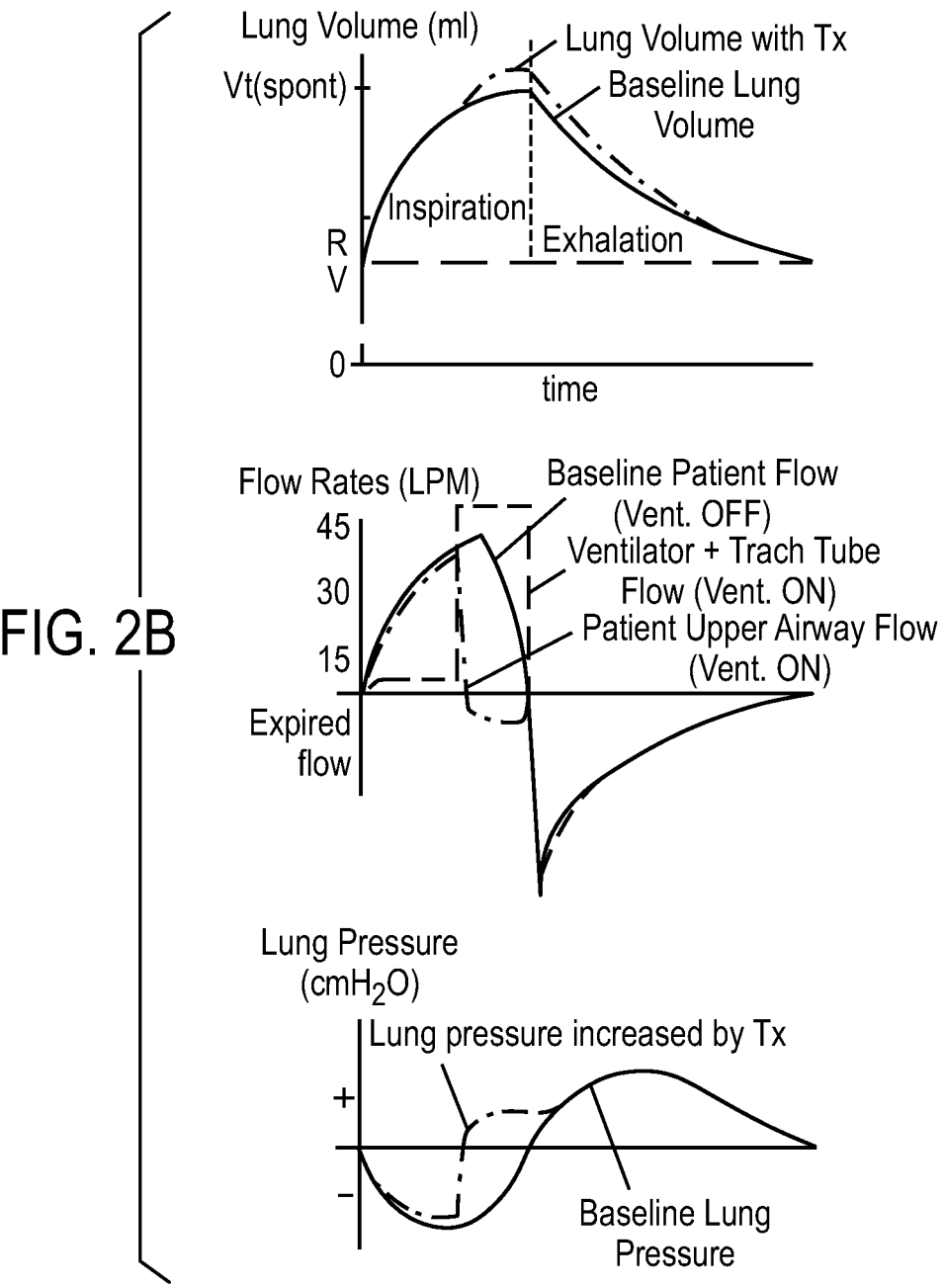
Figure 2C:
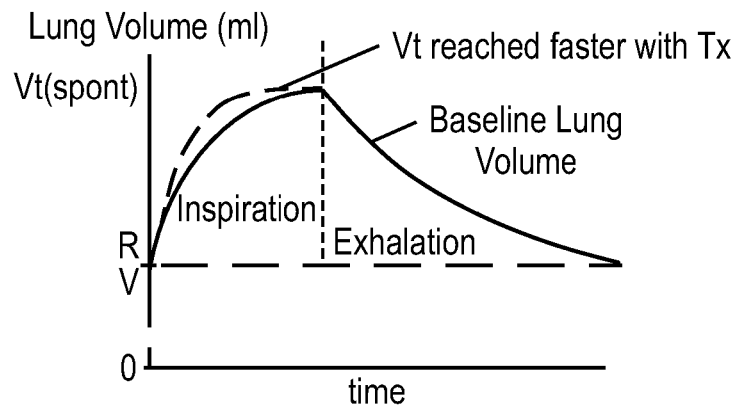
Figure 2C:
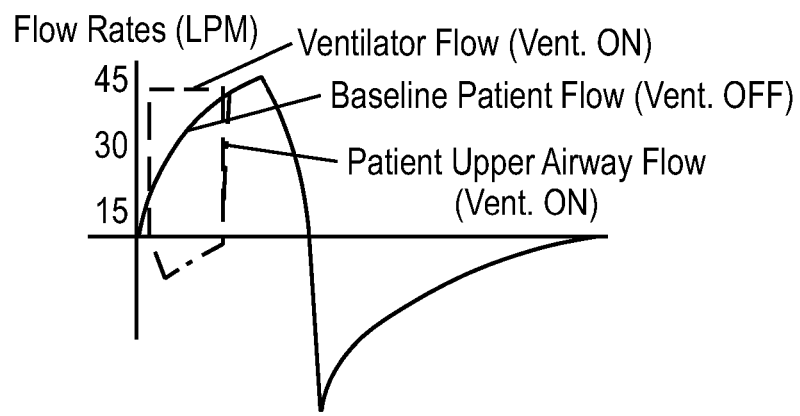
Figure 2C:
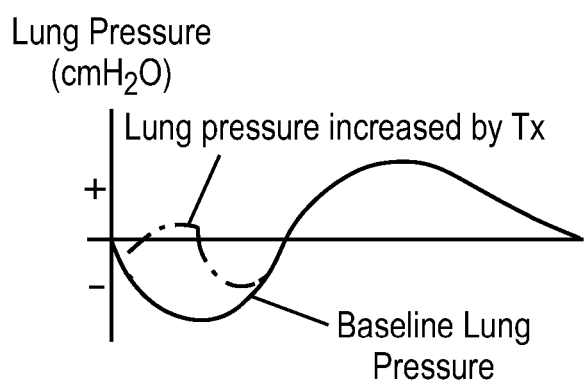

FIGS. 2A-2C show non-limiting examples of how a ventilation system according to embodiments of the invention can support, or perform part or all of, the patient's work of breathing in an open airway system and thus promote activity and ambulation. The patient's work of breathing is assisted by the ventilator gas delivery and entrainment caused by the ventilator gas to exceed the patient's spontaneous breathing flow rate, and thus elevating pressure in the lung. FIG. 2A represents the therapy when it is delivered during the patient's entire inspiratory phase. FIG. 2B represents the therapy when it is delivered at the end of the patient's inspiratory phase with oxygen therapy delivered during the beginning of the patient's inspiratory phase. FIG. 2C represents the therapy when it is delivered at the beginning of the patient's inspiratory phase. Each of these three therapeutic timing options has unique therapeutic effects. In the figures, the solid line represents the indicated parameter without the therapy and the dashed line represents the indicated parameter with the therapy. The top graphs represent the patient's lung volume with and without the therapy, showing residual volume RV and tidal volume Vt. The middle graphs represent the patient's inspiratory and expiratory flow with and without the therapy, and the ventilator's inspiratory flow. The bottom graph represents the resultant lung pressure with and without the therapy.

FIG. 2A shows a representative ventilator output waveform which is generally a square wave during the majority of the patient's inspiratory time. Compared to the baseline condition, this ventilator output inflates the lung faster and at the end of inspiration inflates the lung slightly more. In FIG. 2A, the patient's breath is supported by the therapy throughout inspiration, resulting in an almost neutral pressure condition in the lung, while supplying much of the volume needed by the patient. Compared to conventional ventilation which requires a relatively high positive pressure to be generated in the lung, this open system has the benefit of not requiring such a high lung pressure.

FIG. 2B shows a ventilator output waveform timed with the back end of the inspiratory phase, and compared to baseline, inflates the lung deeper, increasing the tidal volume of the patient, thus, increasing ventilation. To assure achieving the necessary oxygenation, supplemental oxygen is delivered early in the breath. A slight positive lung pressure occurs late in the inspiratory phase.

FIG. 2C shows a ventilator output waveform timed with the front part of the inspiratory phase, and compared to baseline, inflates the lung faster, helping the patient to achieve the needed tidal volume much earlier than without the therapy, thus, keeping the patient's lung distended for a longer period of time thus improving gas exchange. The ventilator can alternate between these three alternative timing modes of FIGS. 2A, 2B and 2C as needed or as desired. Hence, the ventilator described in the invention may be capable of facilitating mobility and even exertion of a patient with respiratory insufficiency without the patient fatiguing, yet in an open airway system.

The respiration support of patient P in accordance with the principles of the invention may preferably be implemented in a system, method, or apparatus that may be compact and/or portable. As shown, for example in FIG. 1A, the respiration support of patient P in accordance with the principles of the invention may be implemented in a system, method, or apparatus that may be wearable or carryable by the patient. The principles of the invention may, however, also be used with other types of ventilation systems. Non-limiting examples of ventilation systems with which the principles of the invention may be used include stationary ventilators, ventilators suitable for use in vehicles, ventilators suitable for home use, ventilators sized for a patient to carry or wheel on a cart, wearable ventilators, carryable ventilators, and central respiratory systems, such as those in medical facilities. The invention may also be applied to oxygen therapy systems and interventional respiratory treatments.

Figure 3:
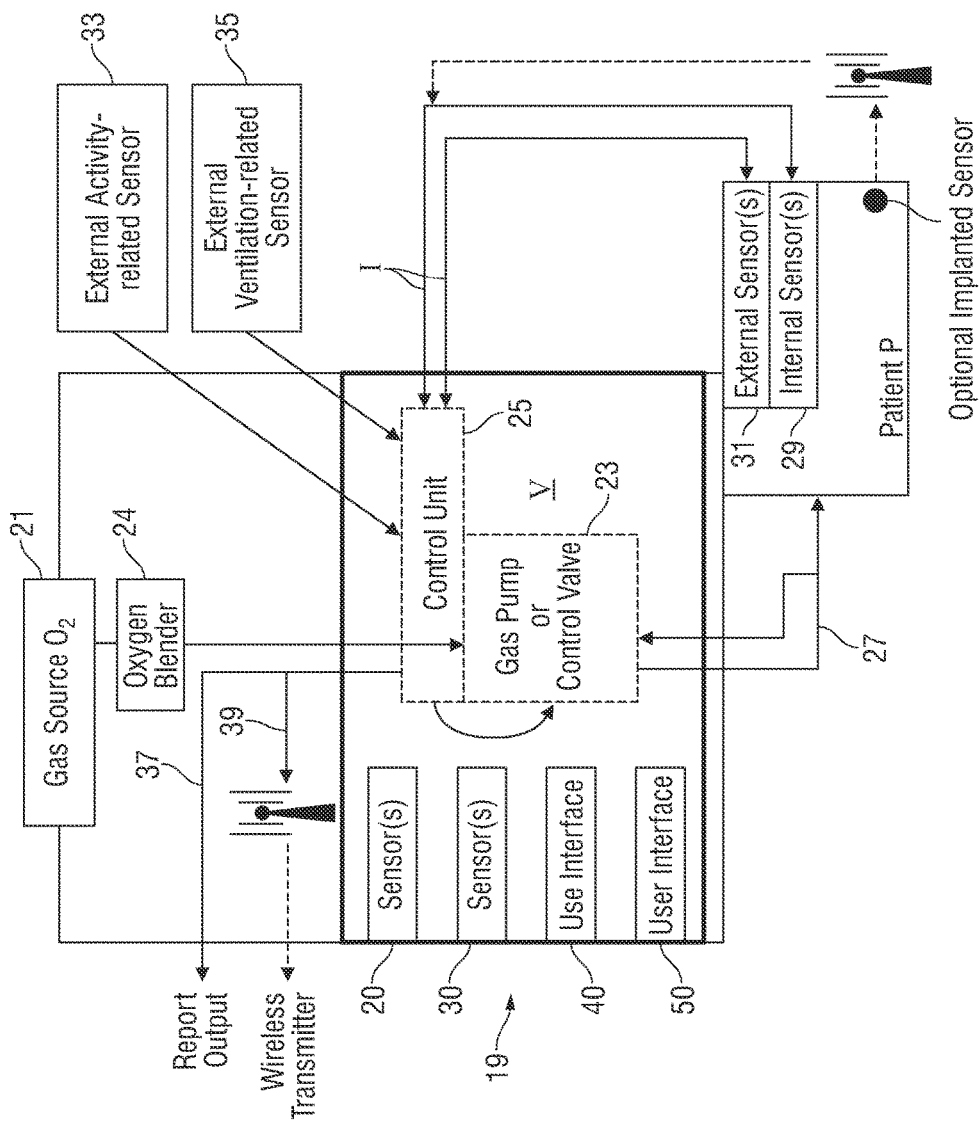
FIG. 3 shows a schematic of a basic embodiment of the invention describing in more detail functional aspects of embodiments of the invention.

An exemplary overall system 19 is illustrated in FIG. 3, indicating ventilator V, gas source $O_2$ 21, gas pump or control valve 23, control unit 25, ventilation catheter or other patient interface 27, one or more internal sensors 29, and patient P. The gas source $O_2$ 21, gas pump or control valve 23, and control unit 25 can be separate or integrated components of the system 19. The control unit 25 may be connected to one or more internal sensors 29 and/or one or more external sensors 31 (as shown in FIG. 1A). The one or more internal sensors 29 may preferably be spontaneous breath sensors. The one or more internal sensors 29 and/or one or more external sensors 31 may be any of the sensors or devices described herein in any combination. Reference numerals 20, 30, 40, and 50 may represent non-limiting examples of sensors and interfaces that may by used with embodiments of the present invention. For example, sensors may be internal activity-related sensors 20, such as actigraphy or a pedometer; ventilation related sensors 30, such as etCO$_2$, SpO$_2$, depth of respiration, or rate of respiration; user interface for well-being scale 40, such as BORG, quality of life, or tiredness scale; or user interface for administering an exercise test 50, such as a six minute walk. It is important to note that, although sensors and interfaces may be integral to or inside the ventilator, as shown in FIG. 3, they may also be modular and operably connected to the ventilator.

The control unit 25 may receive input from internal or external activity-related sensors 20, 33 and/or external ventilation-related sensors 35. The control unit 25 may report output via hardwire 37, wireless transmitter 39 or other suitable procedure. An optional implanted sensor 41 within a patient P may transmit information I via hardwire, wireless transmitter or other suitable procedure. An oxygen blender 24 may be provided between the gas supply 21 and the control valve 23 in order to provide the required or desired concentration of oxygen to the patient. The end-tidal CO$_2$ sensor, or other sensor, can be used to determine the concentration of oxygen being delivered to the patient, and can be used to adjust the blender as necessary. The oxygen can alternatively be bled into the gas delivery circuit to the patient near the outlet of the ventilator V to the gas delivery circuit 27. A breath sensor may provide feedback from a patient P and/or the gas delivery circuit 27 to the control unit 25 and/or control valve 23.

A patient's spontaneous breathing preferably can be detected by way of sensors. A catheter or gas delivery circuit can be used to introduce oxygen-rich gas into the lungs as needed to contribute to work of breathing by performing work on the respiratory muscles as described in FIGS. 2A-2C. As shown in FIG. 1A, the patient's airway may be operably connected to the ventilator via a catheter 5 or gas delivery circuit. The sensors and catheter or gas delivery circuit can be associated with the patient in a variety of ways. For example, as illustrated in FIG. 1A, a catheter 5 or gas delivery circuit may be introduced in the trachea transtracheally, or can be coupled to the channel of a tracheostomy tube.

Alternatively, a catheter 5 or gas delivery circuit may be introduced at other points into a patient P, including, as further non-limiting examples, through the mouth or nose of the patient P (as in FIGS. 1B and 1C), or by positioning the tip of the catheter at the entrance to or outside of the nostrils, or introducing a catheter via an artificially created entry point somewhere on the body and tunneling it internally to and into the trachea. Any other suitable technique may be employed to operably connect the patient's airway to a ventilator. As another non-limiting example of a ventilator system that may be useful with the present invention, the patient's airway may be operably connected to a ventilator using a noninvasive breathing mask and a single or dual limb breathing circuit.

The devices or sensors that provide input to a control unit may be any suitable known devices or sensors, and may be chosen based, for example, on parameters to be measured, system configuration, and patient and system interaction. Devices or sensors may be implanted on or in a patient, worn on or attached to the patient or the patient's clothing, integral to the ventilator, modularly attached to the ventilator, or held by the patient. Numerous devices and sensors may be used in the inventive ventilator system and are described in greater detail below. Non-limiting examples of useful devices and sensors include actigraphy sensors, pedometers, end-tidal CO$_2$ sensors, pulse oximetry sensors and a pulse oximetry sensors with heart rate monitors, spontaneous breath sensors, and intra-tracheal breath sensors. Other useful devices and sensors are known in the art, or may be discovered, which the skilled artisan will recognize as suitable for use with the invention when provided with the teachings herein.

Ventilator systems of the present invention may also preferably include user input interfaces, such as buttons, keypads, touch screens, etc. that preferably facilitate the entering of information or setting of ventilation parameters, therapeutic goals, or overall health goals by the patient or clinician; and output interfaces or devices that preferably facilitate the provision of information by the ventilator system to the patient or clinician. Non-limiting examples of output interfaces or devices include devices, such as alarms, displays, printers, hand-held digital assistants, emails or text messages, etc., that preferably can alert the patient or clinician to an occurrence or condition.

Figure 4:
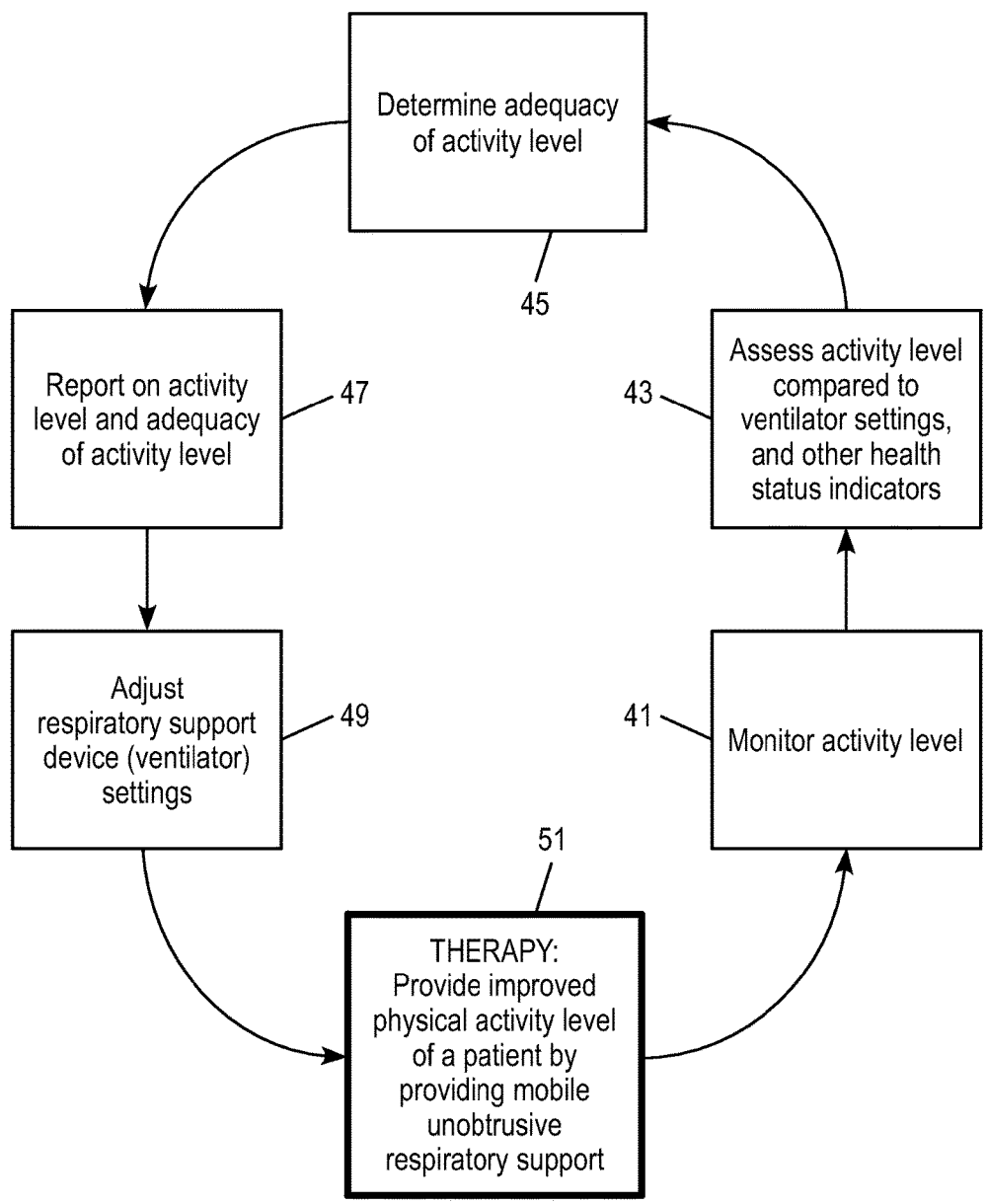
FIG. 4 shows a flow diagram of an embodiment the invention, describing in more detail functional aspects of embodiments of the invention.

The general flow diagram in FIG. 4 shows that patient activity is an important therapeutic goal, and that monitoring, assessing, and reporting on patient activity level is used to meet the therapeutic goal. Ultimately, a determination is made regarding the ventilation parameters, and appropriate action is taken to facilitate obtaining the activity related goals. The functionality of the system of FIG. 4 may be carried out, for example, by the system of FIG. 3.

In FIG. 4, activity level of a patient may be monitored 41. Assessed activity level may be compared to ventilator settings, and other health status identifiers 43. A control unit may then determine the adequacy of ventilation for the activity level 45. The control unit may then report on the activity level and adequacy of the ventilation for that activity level 47. If necessary, the control unit may adjust the ventilator or respiratory support device settings 49. As such, the therapy may be improved by correlating physical activity level with mobile, unobtrusive respiratory support 51.

Respiratory devices may include a control unit that directs the operation of function of the ventilator, such as, for example, providing gas flow to the patient, optionally in synchronization with the patient's breathing. In some embodiments, monitoring and reporting capabilities are provided by enhancing or modifying the capabilities of the respiratory device control unit. Control unit modification and/or enhancement may be provided using any of a wide variety of techniques known to those of ordinary skill in the electronic and software arts. As such, there are numerous alternative ways to enhance the control system capabilities to realize the improved capabilities of the inventive system. Control system modification or enhancement may include all or some of: additional or modified stand alone electronics; additional or modified integrated electronics; additional or modified hardware; additional or modified software; additional or modified firm ware; additional or modified memory and/or additional or modified input/output functionality. Alternatively, one or more additional control units may be added to the respiratory device to provide the inventive monitoring and reporting capabilities. Any additional control unit(s) may preferably work in cooperation with, and share data, such as respiration data, with control unit.

Likewise, known respiratory devices can be modified to perform the monitoring and reporting capabilities of the present invention. The specific component(s) added, system modification(s) or enhancement(s) or degree or combination thereof will depend on the inventive reporting or functionality capability being implemented. A number of non-limiting exemplary monitoring and reporting functions and capabilities that may be implemented by or provided by embodiments of the inventive ventilator systems are described below. Non-limiting exemplary functions and capabilities include activity level monitoring, pedometer feedback and estimation, such as 6 minute walk test data collection and report generation, well being interface, end tidal $CO_2$ monitoring and control system feedback, oxygen saturation monitoring and control system feedback, spontaneous respiration rate monitoring and control system feedback, therapy utilization and compliance monitoring and control system feedback, breathing source gas level/duration monitoring and control system feedback, ventilator auto set-up function, automatic therapy titration, spirometry, and exacerbation detection and prevention, monitoring, and control system feedback.

Figure 5:
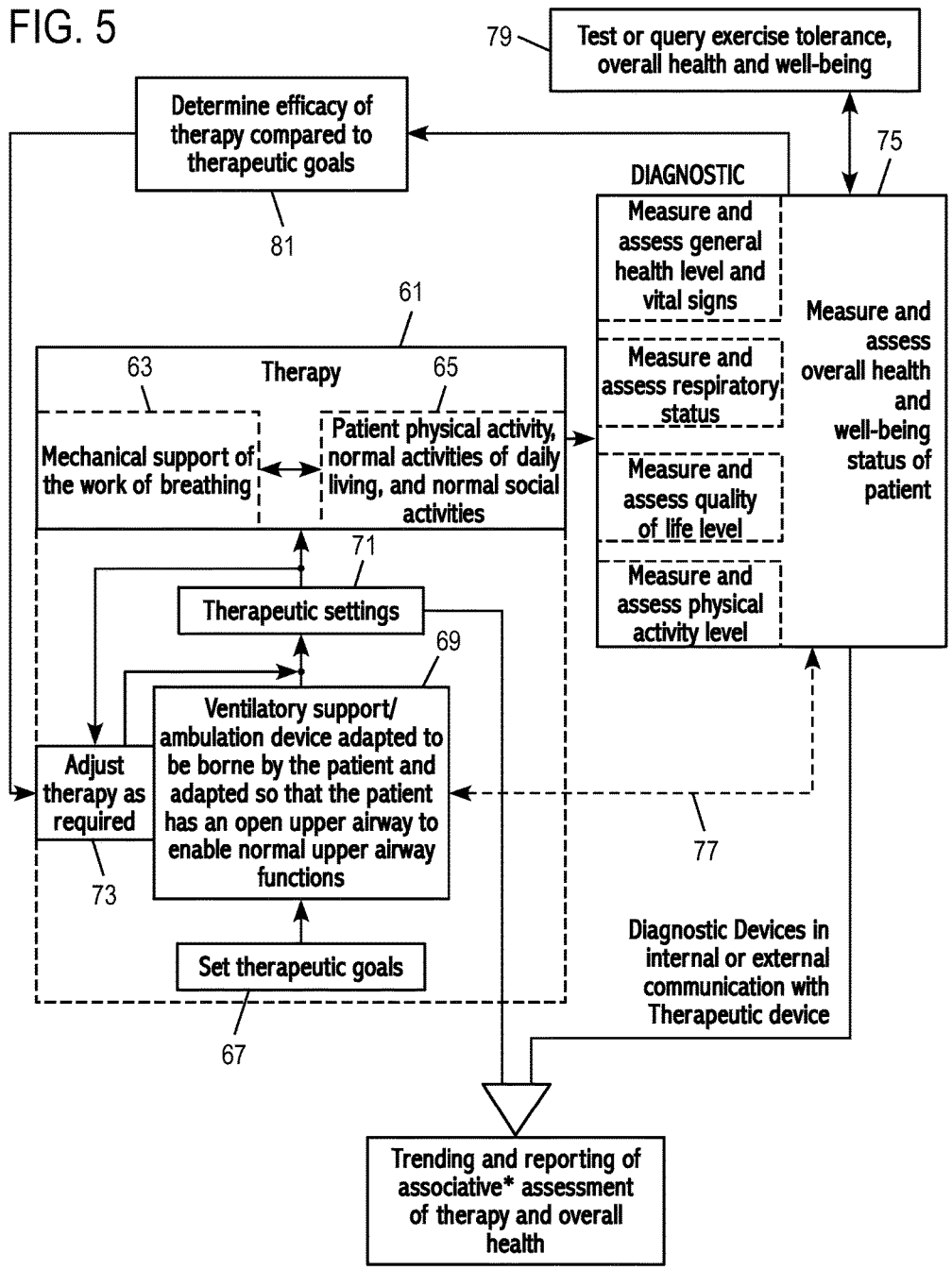
FIG. 5 shows an overall layout of an embodiment of the invention.

FIG. 5 illustrates an overall view of an exemplary embodiment of the present invention, in which various diagnostic assessments and reporting of or interaction with those assessments are made to determine the adequacy of the therapy. Therapy 61 may include mechanical support of breathing 63 administered in relation to patient physical activity, normal activities of daily living and normal social activities 65. Therapeutic goals 67 may be entered to a ventilatory support/ambulation device 69 adapted to be borne by a patient and adapted so that the patient has an open upper airway to enable normal upper airway functions. Therapeutic settings 71 may be used to administer therapy 61. Therapy may be adjusted as needed 73.

Diagnostic devices 75 may be in communication 77, internally or externally, with a therapeutic device 69. The diagnostic device 75 may (1) measure and assess general health level and vital signs, (2) measure and assess respiratory status, (3) measure and assess quality of life level, and/or (4) measure and assess physical activity level for the purposes of measuring and assessing overall health and well-being status of a patient. A test or query 79 may be presented to examine exercise tolerance, overall health and well-being. Efficacy of the therapy compared to therapeutic goals may be determined 81.

Capability to Improve Overall Health

Overall health (such as activity, quality of life, dyspnea, comfort, exacerbation frequency, exercise tolerance, spontaneous respiratory rate, number of steps taken per day, etc.) can be improved by the ventilation system of this invention because the ventilator is designed to be borne by the patient, and designed to provide mechanical ventilatory support using an open airway ventilation system. Therefore, the ventilator enables activities of daily living, such as normal use of upper, being able to ambulate and move, and being able to exert oneself without immobilizing levels of dyspnea.

Overall Health Measurements

Overall health measurements (such as activity level, quality of life scales, dyspnea scales, comfort scales, disease exacerbation frequency, exercise tolerance, spontaneous respiratory rate, number of steps taken per day, etc.), conventionally are measurements that are made manually. With respect to mechanical ventilation, these types of measurements have not been made as part of a ventilation system, since conventional ventilators are not used to improve or optimize the patient's overall health. Conventional ventilators, when used for respiratory support, have historically been used only to optimize the patient's blood gases and other respiratory parameters, but not overall health. The system of this invention includes the capability of measuring and assessing these overall health indicators.

Capability to Set Goals for Overall Health

With existing conventional ventilation systems, the prescribing physician cannot and has no need to set goals for the patient's overall health. The only goals that are set are the ventilator parameters, the goal of physiologic stability and, if possible, weaning from the ventilator. But overall health, such as activity level, quality of life measures, and exacerbations are not measured as part of the ventilation therapy, nor are goals set for these parameters. A ventilator is not considered in this context. However, with a mobility assist device, such as the ventilator of this invention, the physician has the ability to consider the patient's overall activity level and health as part of what the therapy accomplishes. The physician can then set a goal as part of the intended therapy. Therefore, when the patient is initially prescribed the therapy of this invention, the doctor, and optionally the patient too, can set overall health goals, along with the ventilator settings. The goals can adjust over time as appropriate for the patient, given the prevailing circumstances. For example, a patient with a chronic and progressive disease, the goals may decrease very slightly every year. A patient with a chronic but non-progressive disease, the goals may slightly increase every year or every month. In contrast, if the patient where using a conventional ventilation therapy, their goals (if it where possible to set them and track them, which it is not) would significantly decrease every year or stay the same, for a progressive disease and non-progressive disease respectively.

Trending and Reporting

The overall health measurements and ventilation parameters can be tracked, trended and reported. They can be stored for retrospective reporting or analysis purpose, for utilization reviews, for care providers and home care equipment providers to help them manage their patients. The reports and trending can be reported automatically to the physician so the physician can manage the patient remotely. The data can be reviewed periodically to detect trends in the patient's well being, and to interdict if and when necessary.

Associativity Between Overall Health Goals and Ventilator Parameter Settings

Setting and tracking overall health goals with a ventilation system is possible with embodiments of the present invention such that the overall health goals and ventilation parameters can be tied together. If the overall health goals are not being met, the ventilation parameters can be adjusted or re-titrated, usually increasing the therapeutic level of the ventilation parameters, in attempt to meet the overall health goals. Conversely, if the overall health goals are being met, the ventilation parameters can be re-titrated or turned down, in order to reduce the patient's dependency on the mechanical ventilation, while still meeting the ultimate goals of the therapy, which is a certain level of overall health. Also, turning down the therapy when the overall health goals are being met helps conserve oxygen and is more cost effective in the long run. The adjustment or re-titration of the ventilation parameters can be automatic, semi-automatic, or manual, or any combination of thereof. The associativity can be set up in advance when prescribing the therapy to the patient, or can be established or re-established during the course of therapy, for example every month, and can be set up manually or wirelessly.

Health Status Index

With the advent of a mobility enhancement ventilator, setting overall health goals, and associativity between overall health and ventilator parameters, a new clinical measure may be possible that was not possible before. The new clinical measure may be a Health Status Index (HSI), which is a dimensionless parameter that takes into account the level of therapeutic support the patient is receiving and the overall health of the patient. The HSI can be expressed in an absolute scale, but can also be expressed in a percent predicted scale, or a percent of target scale. For instance, a patient may have an HSI of 8 out of a maximum of 10 using a 0-10 or −10 to +10 scale. Their predicted value might be a 7, giving them a HSI percent predicted of 114%, meaning they have over-achieved the normal value for that patient type. Their target value might have been 8, giving them a HSI percent of target of 100%. The HSI can be for example a numerator of Overall Health and a denominator of therapeutic level. For example, the numerator would include overall health subcomponents (such as activity level, comfort, dyspnea, number of steps per day, RR, and speech quality), each with a relative weighting of importance relative to the other subcomponents, and the denominator would include therapeutic level subcomponents (such as oxygen percentage setting, ventilator volume setting, number of hours used per day), each with a relative weighting of importance relative to the other subcomponents. The HSI can include a more complex formula as well, and a wider scale than 1-10 or −10 to +10. The HSI can also be a value that has units associated with it, rather than unit-less as described above, such as 0.8 steps per day per ml per hour per % oxygen. Defining an HSI goal, and tracking to that goal, and adjusting the therapy to meet that goal, is one of the ultimate goals of the therapy.

Figure 6:
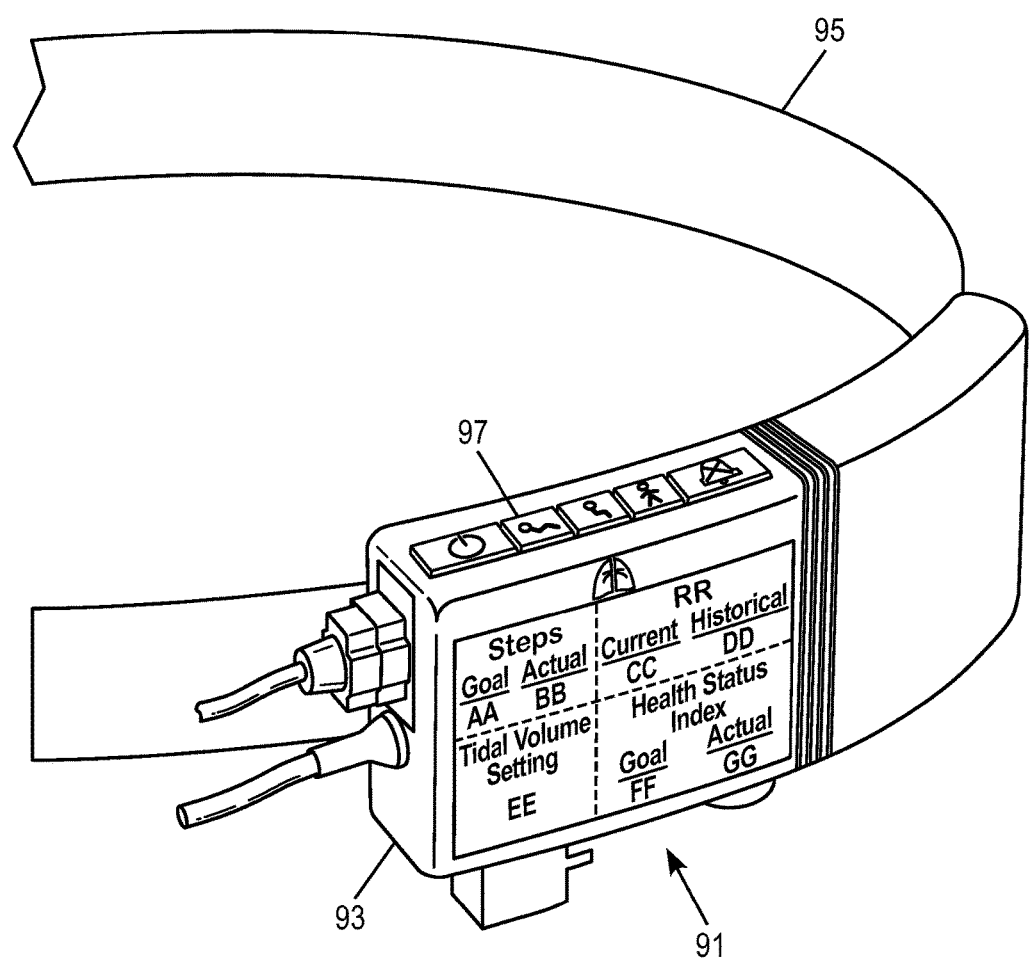
FIG. 6 shows an exemplary ventilator and ventilator-user interface and belt system to fasten the ventilator to the user, which are useful with embodiments of the present invention.

FIG. 6 shows an exemplary ventilator 91 and ventilator-user interface 93 and belt system 95 to fasten the ventilator 91 to the user, which are useful with embodiments of the present invention. The user interface 93 may include displays, indicators, alarms, etc. The ventilator 91 may include input devices, such as buttons, touch screens, keypads, etc. Inputs 97 may allow for turning power on/off, entering activity levels, turning alarms on/off, and other options.

Figure 7:
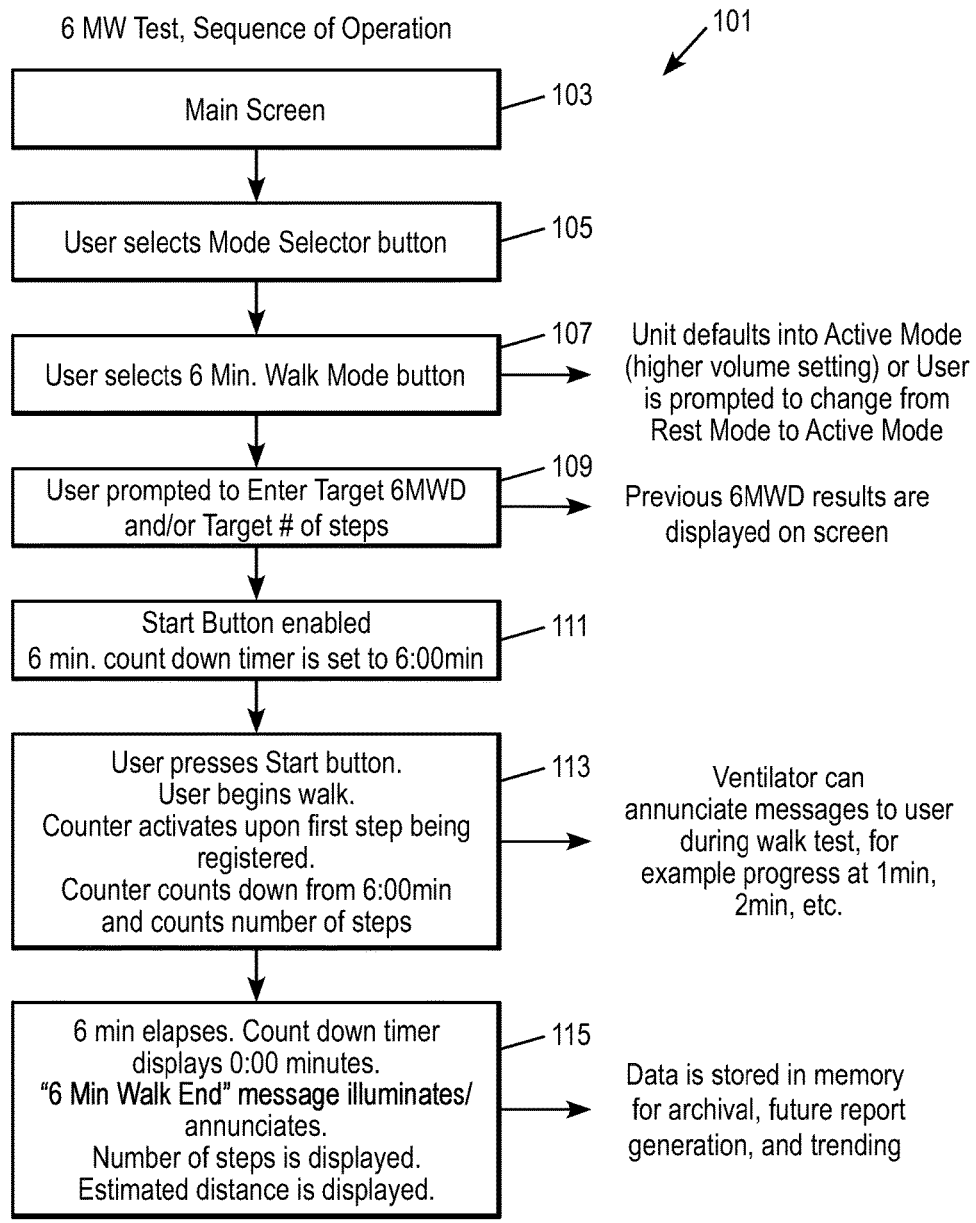
FIG. 7 is a flow chart describing the administration of an exercise test, particularly in this case a six minute walk test, using the interface and interactive features that may comprise an embodiment of the present invention.

FIG. 7 is a flow chart describing the administration of an exercise test 101, particularly in this case a six minute walk test, using the interface and interactive features that may comprise an embodiment of the present invention. From a main screen 103, a user may select a mode 105. In an exemplary embodiment, the user may select a six minute walk test 107, wherein the unit defaults to active mode (higher volume setting) or a user may be prompted to change from rest mode to active mode. A user may be prompted to enter a target six minute walk distance and/or a target number of steps 109. A start button or other user input may enable a countdown 111. The user may press a start or other user input and begin walking 113, wherein the counter is activated upon the first step and registers the number of steps and/or counts down the remaining steps. In certain embodiments, the ventilator may enunciate messages to a user during the test, such as time remaining. At the conclusion of the test, a display may indicate completion of the test and display relevant information 115. Data may be stored in a memory and/or processed by a processor.

Figure 8:
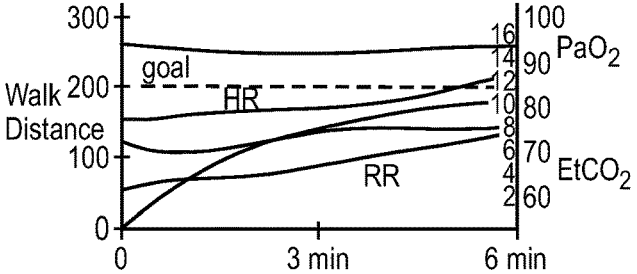
FIG. 8 shows a non-limiting example of report that certain embodiments of the present inventive ventilator system may be capable of generating.

FIG. 8 shows a non-limiting example of report that certain embodiments of the present inventive ventilator system may be capable of generating. Reports 121 may include patient information 123, ventilator settings 125, test results 127, history 129, and other relevant information. Information may include text, graphs, charts, graphics and other visual or auditory indicators.

Figure 9:
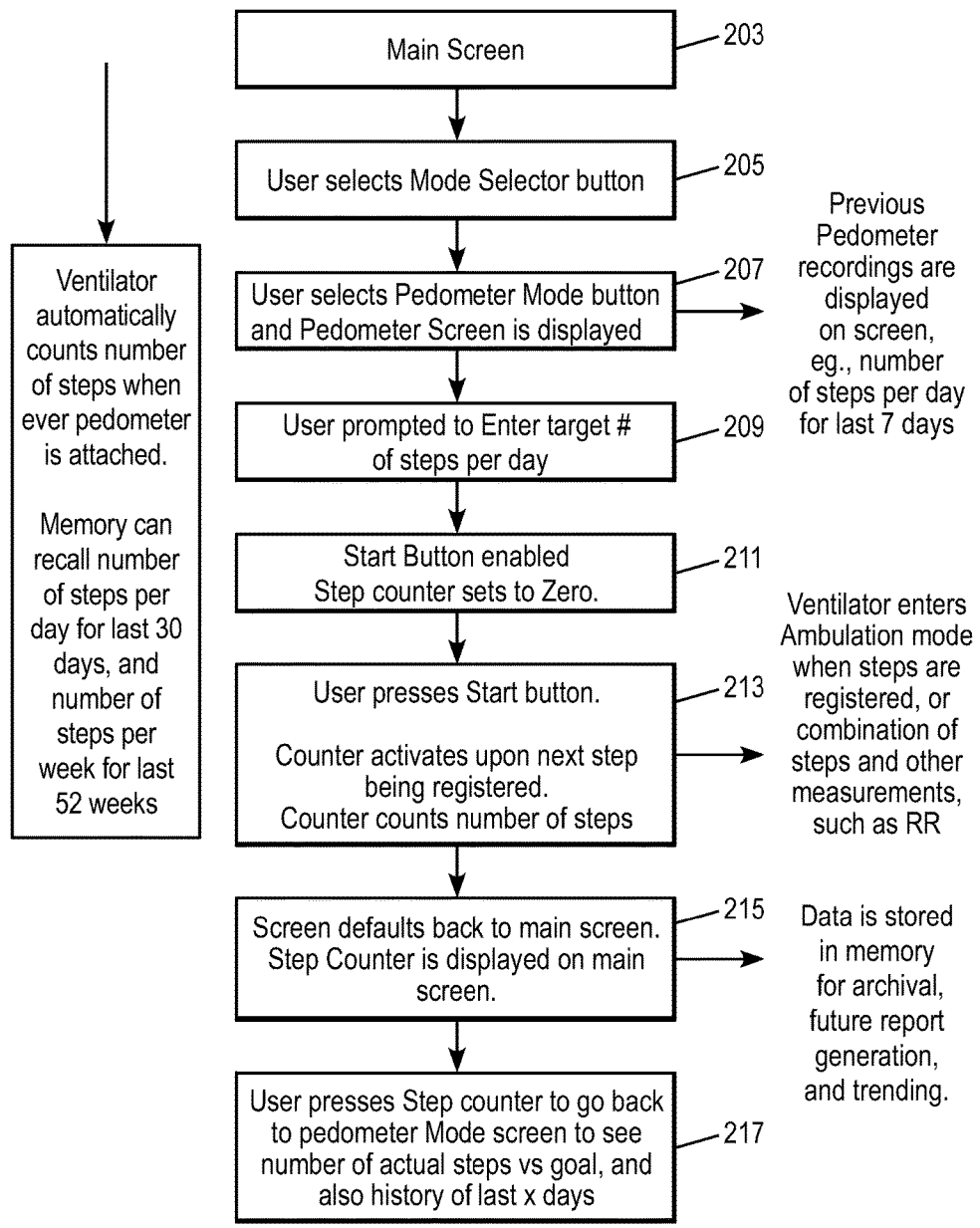
FIG. 9 shows a non-limiting example of the use of a patient activity-related monitoring function of certain embodiments of the present inventive ventilator system, particularly in this non-limiting exemplary case, a pedometer.

FIG. 9 shows a non-limiting example of the use of a patient activity-related monitoring function of certain embodiments of the present inventive ventilator system, particularly in this non-limiting exemplary case, a pedometer. From a main screen 203, a user may select a mode 205.

In an exemplary embodiment, the user may select a pedometer mode 207, wherein pedometer recordings are displayed. The ventilator may automatically count steps when a pedometer is attached and may store results in a memory. A user may be prompted to enter a target number of steps 209. A start button or other user input may set a counter to zero 211. The user may press a start or other user input and begin walking 213, wherein the counter is activated upon the first step and registers the number of steps or combination of steps and other measurements, such as respiration rate. In certain embodiments, the ventilator may enter ambulation mode when steps are registered. In certain embodiments, the screen defaults back to the main screen and a step counter may be displayed on the main screen 215. Data may be stored in a memory and/or processed by a processor. The user may enable a user input to go back to pedometer mode to see the actual number of steps versus a goal and a history 217.

Figure 10:
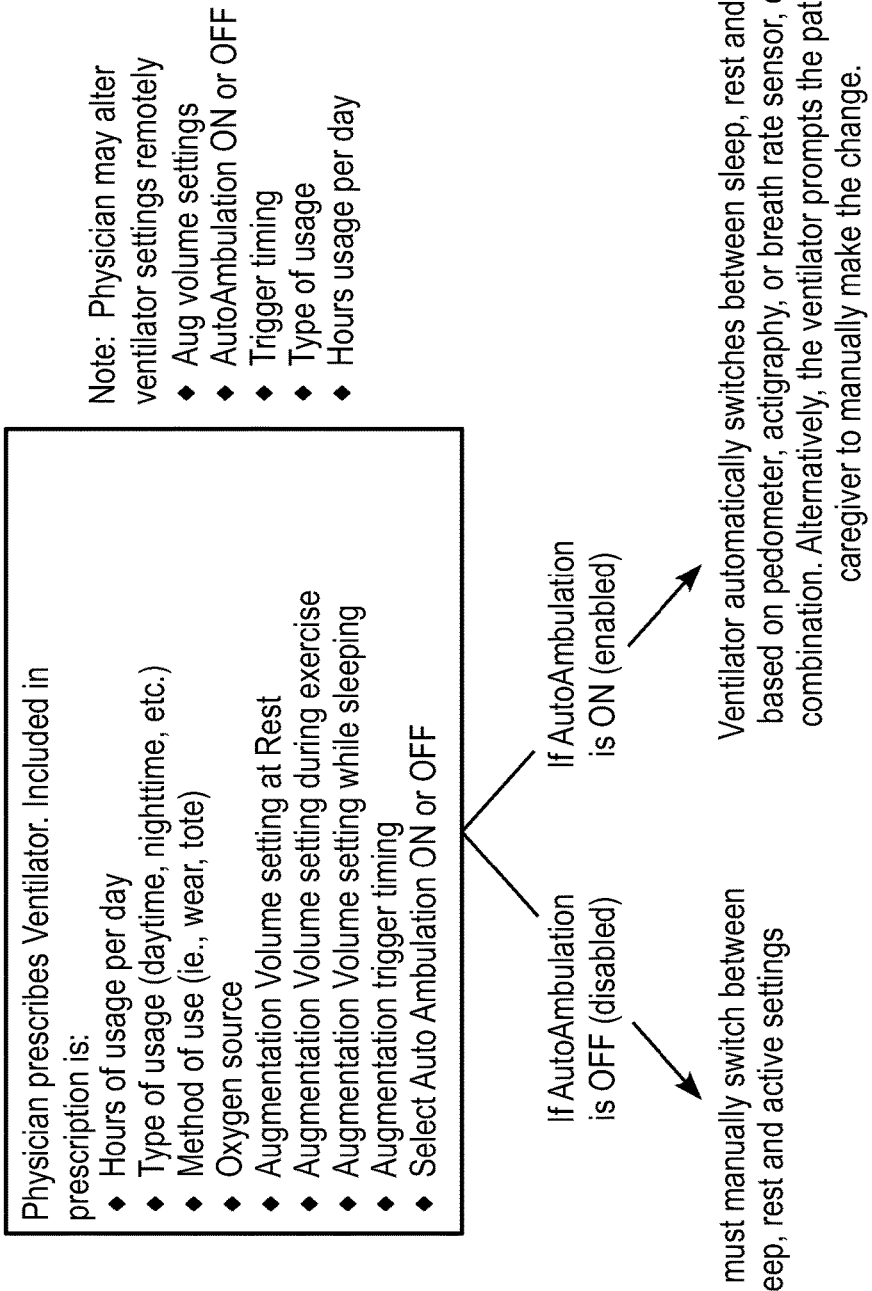
FIG. 10 shows a non-limiting example of the use of an auto-adjustment function of certain embodiments of the present inventive ventilator system, particularly in this non-limiting exemplary case, an auto-ambulation mode in which the ventilator output responds to the ambulation level of the patient.

FIG. 10 shows a non-limiting example of the use of an auto-adjustment function of certain embodiments of the present inventive ventilator system, particularly in this non-limiting exemplary case, an auto-ambulation mode in which the ventilator output responds to the ambulation level of the patient. If auto-ambulation is off, a user must manually switch between sleep, rest and active settings. If auto-ambulation is on, the ventilator automatically switches between sleep, rest and active based on readings from one or more sensors or a combination thereof. Alternatively, the ventilator may prompt the patient or caregiver to manually make the change.

Figure 11:
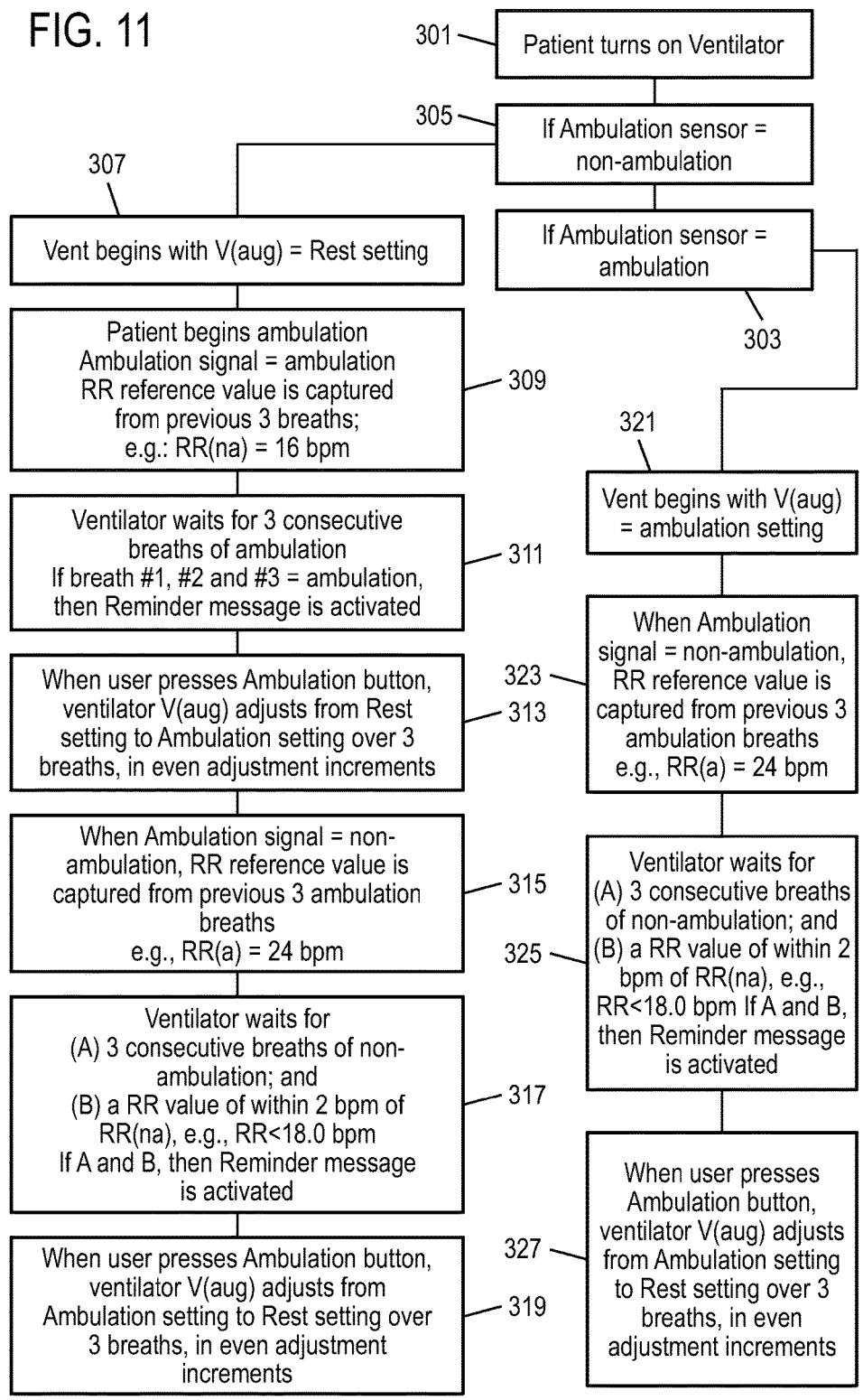
FIG. 11 is a flow chart showing an auto-adjustment function of the ventilation parameters based on patient need, according to an exemplary embodiment of the present invention.

Multiple types of sensors may be used to collect data regarding a patient and analyzed together to make a determination of patient status. In preferred embodiments, a breath sensor may be used in combination with an activity sensor or health sensor. The information from both types of sensors can be analyzed together to adjust ventilation, as needed. One exemplary embodiment may be the system and method as shown in FIG. 11. FIG. 11 is a flow chart showing ambulation monitoring according to an exemplary embodiment of the present invention. Initially, a patient or physician may turn a ventilator on 301. If the ambulation sensor detects non-ambulation 305, then the ventilator begins augmentation for a rest setting 307. If a patient then begins ambulation 309, the ambulation signal is equal to the ambulation respiratory rate reference value captured from, for example, the previous three breaths. The ventilator may wait for a predetermined number of breaths within a predetermined time. For example, the ventilator may wait for three consecutive breaths at an ambulation level, where there are a set number of breaths per time period, such as one breath every three seconds. If these breaths indicate ambulation, then a reminder to the patient is activated 311. If and/or when the user selects ambulation, the ventilator may adjust from rest to ambulation over a set number of breaths 313, for example, three breaths in even adjustment increments. Adjustment may also be automatic. When an ambulation signal indicates non-ambulation, the respiratory rate reference value is captured from a previous number of breaths 315. The ventilator may wait for a set number of consecutive breaths of non-ambulation and/or a respiratory rate value of within a set number of breaths per minute 317. Results may be compared across sensor types. For example, breath sensors may indicate non-ambulation, and this could be confirmed or disputed by an activity level sensor. The control unit may compare values from various sensor types and make a determination of patient activity level and/or health status. Other times a sensor may malfunction or give a false reading, and the other sensor type may compensate. If a threshold limit is met, then a reminder may be activated. This may also be done automatically. When the user selects a rest setting, the ventilator adjusts to a rest setting over a set number of breaths, preferably in even increments 319.

If the ambulation sensor detects ambulation, then the ventilator is set on an active or similar setting 303. The ventilator begins augmentation for an ambulation setting 321. When an ambulation signal indicates non-ambulation, the respiratory rate reference value is captured from previous number of breaths 323. The ventilator may wait for a set number of consecutive breaths of non-ambulation and/or a respiratory rate value of within a set number of breaths per minute 325. If a threshold limit is met, then a reminder may be activated. This may also be done automatically. When the user selects a rest setting, the ventilator adjusts to a rest setting over a set number of breaths, preferably in even increments 327.

It may be preferable to include multiple sensor types to confirm reading prior to adjusting therapy. For example, an activity sensor may not register movement if a patient is active on a stationary exercise machine, but a breath sensor would indicate an active status. Therefore, multiple sensors may allow for more accurate detection and analysis of patient status and respiratory need than a single type of sensor. Information from multiple sensors may allow matching of measurements by the control unit and more accurate detection of patient activity and overall health.

The following sections describe various exemplary embodiments and aspects of the inventive ventilator system, sensors, and methods of use. Any of the embodiments and aspects of the inventive ventilator system, sensors, and methods of use may be used in combination with any other embodiments and aspects.

Actigraphy Sensor and Monitoring Function

Ventilator systems according to the present invention may preferably have the capability of determining and/or monitoring the patient's activity level(s). Determination and monitoring of the patient's activity level(s) can be accomplished, for example, through the use of actigraphy sensor(s). Together with other ventilator information, readings, measurements and settings, such as sleep, rest, active, information regarding the patient's activity level(s) can be useful in titrating and optimizing the ventilation therapy, as well as managing the patient, and monitoring the efficacy of the therapy.

The actigraphy sensor(s), the control unit(s) of the ventilator, input and output devices, and other types of sensors, acting alone or in cooperation preferably have the ability to determine or provide one or more of, or any combination of, the following types of information: average activity level; current activity level; last set time period activity level; activity level trend; activity level goal setting, and comparison of actual against goal; activity level alerts (alert if too low, alert if goal exceeded); activity level reported with correlation to other parameters (e.g., vol. setting, respiratory rate, time of day, etc.); activity level graphical display versus time; activity level feedback to control settings (e.g., vol. setting); and/or report generation.

The actigraphy sensor(s) may be integrated into the ventilator, but alternatively may be modular. The particular configuration that is more preferable may be determined by, for example, the type of ventilator. For example, an integrated sensor may be particularly desirable when the ventilator is wearable ventilator. When the ventilator is not worn by the patient, but is, for example, carried, wheeled, or even stationary, the actigraphy sensor(s) preferably can be modular, such that the patient can wear the sensor in order for it to better record the patient's activity level. It may be useful for the patient to wear the actigraphy sensor(s) during periods when the ventilator is not operably connected to the patient or is not providing ventilation. This would facilitate the determination of a baseline value for the patient's activity level while the patient is not receiving ventilation. It may be preferable for a modular actigraphy sensor(s) to include the ability to store information and later transfer it to the ventilator's control unit upon connection, so that the baseline data may be to determine ventilator settings, and therapeutic values may be synchronized.

Pedometer Sensing

Based on a pedometer sensor or sensors, the ventilator may have the capability of determining the patient's ambulation level. Together with other ventilator information and settings, and patient well-being parameters and optionally clinical parameters, the information can be useful in titrating and optimizing the therapy as well as managing the patient, and monitoring the efficacy of the therapy. The sensor and ventilator may have the ability to provide various modes such as:

Pedometer counter mode where the ventilator registers and/or records: total number of steps over a period, such as steps per day; quickness of walking (no walking, slow walking, fast walking); average steps per period; current steps per period; last time period number of steps; number of steps trend; number of steps goal setting, and comparison of actual against goal; number of steps alerts (alert if too low, alert if goal exceeded); number of steps reported with correlation to other parameters (e.g., vol. setting, respiratory rate, time of day, etc.); number of steps graphical display versus time; number of steps feedback to control settings (e.g., vol. setting); estimated distance for the above, based on selected stride distance; and/or report generation (electronic and hard copy).

Six minute walk test monitoring mode (steps and estimated distance) where the ventilator has a user interface to administer test and display/report results, and registers and/or records: goal setting; results history; countdown timer, prompts and visual/audible indicators (such as "pace is 100 steps per minute", or "good job", etc.); estimated distance function (estimates distance from stride length entered by user); comparison against 6 minute walk with ventilator off (ventilator receives input from standalone pedometer used by patient without the ventilator, or the Ventilator OFF results are entered into the ventilator by user); and/or report generation (electronic and hard copy).

Auto-Ambulation Mode may allow the ventilator to adjust the therapeutic level based on the ambulation level as determined by the pedometer. A physician may set the following: "at rest" volume/timing setting; "exertion" volume/timing setting (the exertion setting can be an "ambulation" setting with multiple levels, for example ambulation 1, ambulation 2, ambulation 3, etc.); optionally, other settings such as sleep, max exercise, conserve, quite, etc.; a pedometer threshold setting; and/or enable auto-ambulation using physician-only key. If the patient's pedometer value is above the threshold setting, the ventilator automatically switches from "at rest" to "exertion" settings. If the patient's pedometer value is below the threshold setting, the ventilator automatically switches from "at rest" to "exertion" settings. A patient can optionally override the "exertion" setting if needed. If programmed by the care provider, the patient can switch to "exertion" settings even if not exerting. The threshold values can dynamically adjust, based on recent activity or trends. The dynamic adjustment range can be pre-determined, determined and set by the physician, manually set, or automatically determined. The auto ambulation mode can also be used with the actigraphy sensor in addition to or instead of the pedometer sensor.

A manual ambulation mode may allow a user to manually switch between the "at rest" settings, and the "exertion" settings. The exertion setting can be an "ambulation" setting with multiple levels, for example ambulation 1, ambulation 2, ambulation 3, etc. These settings are prescribed settings programmed in to the ventilator upon dispensing the ventilator to the patient by the care provider. The manual ambulation mode can also be used with the actigraphy sensor in addition to or instead of the pedometer sensor.

A well-being scale function, such as BORG Scale, comfort scale, dyspnea scale, tiredness scale, ease of breathing scale or quality of life scale may collect and store information. The information collected and made available in this mode can be used along with the ventilator settings and other patient information including patient activity or ambulation level and clinical parameters to determine and track the efficacy of the therapy, and to potentially make adjustments to the therapy. The ventilator may have a built-in user interface menu for user to enter values or to answer questionnaire or survey in order to register/record how the patient is doing or feeling.

An end-tidal $CO_2$ monitoring and feedback function may utilize a sensor. The ventilator has an integral or modularly attached end-tidal $CO_2$ sensor. Based on the sensor, the ventilator may have the capability of determining the patient's ventilation efficiency and gas exchange. Together with other ventilator information and settings, and patient activity level and well-being information and optionally other patient clinical information, the information can be useful in titrating and optimizing the therapy as well as managing the patient, and monitoring the efficacy of the therapy. The sensors and ventilator may have the ability to accomplish the functions and values described herein.

$EtCO_2$ values can be displayed, stored, trended, and provided in a report. $EtCO_2$ reporting can be reported with other information such as ventilator parameters, other monitored values such as pedometer reading, etc. $EtCO_2$ values can be used to automatically or manually adjust ventilator output, for example to go from rest mode to active mode. $EtCO_2$ values can be continuously measured and displayed. $EtCO_2$ values can be reported as exhalation phase values, or inspiration phase values, or both exhalation and inspiration phase values, or an average value of inspiration and expiration. $EtCO_2$ values can be reported as ml $EtCO_2$/ml tidal volume, or as a percentage of tidal volume, or can be normalized to or reported as a function of the breath rate or minute volume or breathing pressure, or breathing flow rate, or I:E ratio, or residual volume.

Oxygen saturation monitoring and feedback function may utilize a sensor. The ventilator may have an integral and/or modularly attached pulse oximetry sensor. Based on the sensor, the ventilator may have the capability of determining the patient's ventilation efficiency and gas exchange. Together with other ventilator information and settings, and patient activity level and well-being information and optionally other patient clinical parameters, the information can be useful in titrating and optimizing the therapy as well as managing the patient, and monitoring the efficacy of the therapy. The sensors and ventilator may have the ability to provide the following functions and values: $SpO_2$ values can be displayed, stored, trended, and provided in a report. $SpO_2$ reporting can be reported with other information such as ventilator parameters, other monitored values such as pedometer reading, etc. $SpO_2$ values can be used to automatically or manually adjust ventilator output, for example to go from rest mode to active mode. A pulse oximeter may also provide heart rate.

Spontaneous respiration rate sensing function may utilize sensors. The spontaneous breath sensors integral to the ventilation catheter and ventilator, continuously un-interruptedly record the spontaneous breath rate of the patient. Based on the sensor, the ventilator may have the capability of determining the patient's spontaneous respiration rate. Together with other ventilator information and settings, and patient activity level and well being information and optionally other patient clinical parameters, the information can be useful in titrating and optimizing the therapy as well as managing the patient, and monitoring the efficacy of the therapy. The sensors and ventilator may have the ability to determine or provide the following functions and values: The spontaneous breath rate ($RR_{spont}$) is displayed, stored, trended and provided in a report. $RR_{spont}$ reporting can be reported with other information such as ventilator parameters, other monitored values such as pedometer reading, etc. $RR_{spont}$ values can be used to automatically or manually adjust ventilator output, for example to go from rest mode to active mode.

Depth of breathing monitoring function may utilize sensors. Using intra-tracheal breath sensors, the depth of spontaneous respiration is recorded. Based on the sensor, the ventilator may have the capability of determining the patient's ventilation efficiency and gas exchange, as well as distress level or activity level. Together with other ventilator information and settings, and patient activity level and well being information and optionally other patient clinical parameters, the information can be useful in titrating and optimizing the therapy as well as managing the patient, and monitoring the efficacy of the therapy. The sensors and ventilator may have the ability to determine or provide the following functions and values: depth of respiration can be correlated to tidal volume, and the type of breathing (at rest, sleep, exertion, exercise). The breath sensor signal can be correlated with a reference spirometry value to provide an accurate estimate of the tidal volume. Depth of breathing can be used to determine health status and ventilator settings.

Therapy utilization and compliance function may utilize sensors. Based on the various sensors, the sensor(s) and ventilator may have the ability to determine utilization and compliance as a function of activity level and well being level. The ventilator may have the ability to record frequency and duration of use of the therapy. Use of therapy can be recorded and reported as a function of hours per day, hours per week, etc., and can be organized into subcategories such as hours at "rest" setting and hours at "exercise" setting, etc. Target values (prescribed by clinician), for example how many hours of therapy per day, can be entered into the ventilator, and actual therapy can be tracked and reported in comparison to target value. Alerts can be enabled if the actual therapy durations are shorter or longer than prescribed values, or if the therapy is not being used at the correct time of the day.

Oxygen source level (duration) monitoring function may utilize sensors. A user may enter oxygen pressure or oxygen cylinder size of the source. The ventilator may track patient breath rate, which is the ventilator rate, and the ventilator volume setting, and provides a displayed value of duration of oxygen source remaining. Remaining time alert may be activated based upon a user entering a threshold setting, for example 30 minutes. At such time, the ventilator alerts the user when 30 minutes of oxygen is remaining.

Ventilator auto-set up function may require a user to enter patient information, such as height, weight, oxygen therapy flow rate prescription, minute ventilation requirement, tidal volume requirement. The ventilator volume setting may then be automatically adjusted to the entered patient information.

Automatic therapy titration function may involve ventilator volume and timing setting automatically adjusted based on patient's breathing profile. For example, a steep spontaneous inspiratory flow curve may adjust the ventilator timing to trigger early and strong, versus a shallow spontaneous inspiratory flow curve that may adjust the ventilator timing to trigger with a delay and at a lower amplitude delivery flow rate, pressure or volume.

A spirometry function may allow the ventilator to estimate the depth of breathing or tidal volume by the intra-tracheal breathing signal collected by the breath sensors. A patient may need a correlation factor of breath sensor signal to breathing volume which is performed when the ventilator is prescribed and provided to the patient. The ventilator can estimate residual volume by correlating tracheal gas composition, breath rate, tracheal breathing gas flow rate, and oxygen volume delivery to lung volume.

Exacerbation detection and prevention may allow the ventilator, based on clinical indicators, predicts the onset of a COPD exacerbation. Once the exacerbation is predicted in advance, the ventilator can take action to help prevent the exacerbation from occurring: the ventilator can remotely notify a clinician to intervene; for example provide the appropriate medication to prevent the exacerbation from taking place; the ventilator can change its settings to provide more ventilatory support or more oxygen to prevent or minimize the exacerbation; and/or the ventilator can automatically or semi-automatically introduce a medication through the breathing circuit or ventilation catheter into the patient's airway in response to the exacerbation detection and after satisfaction of the requisite threshold values. Exacerbations can be predicted by frequency of coughing, type of cough, mucus production level, breath rate, activity level, $SpO_2$, $EtCO_2$, depth of breathing, or other clinical parameters. The ventilator can archive patient parameters or events, and correlate the archived parameters of the last 24 hours to the exacerbation, after the exacerbation has occurred. This can be done automatically by the ventilator or the correlation can be prompted by the clinician. The patient then has his/her individual signature for predicting an exacerbation. A coughing detection system, or bronchospasm detection can optionally be included independent of the exacerbation detection system. The cough and bronchospasm events can be measured, recorded, trended and reported to a user or clinician for use in determining the appropriate intervention.

A vibration alarm function may be provided. Because the patient may be using the ventilator in public while the patient is being active and mobile, and since the patient may be wearing the ventilator, it may be desirable to have a vibration setting for alarms to avoid disturbing other people with audible alarms. The ventilator can optionally include a feature to sense if the ventilator is being worn, versus being toted. If toted, the ventilator can command the vibration alarm setting function to be disabled. The vibration setting can optionally convert to an audible alarm if the vibration alarm is not responded to in a pre-determined time frame.

Table 1 is an example of monitored "Activity Level" performed by a ventilator, including activity level trending, along with other indices such as "Exacerbations". Table 1 indicates the data recorded or received by the system as a direct input from a device, sensor or user input. Information such as that found in Table 1 may be stored, reported or used in any of a number of different ways. The information in Table 1 may be stored in memory available as part of the ventilator electronics. The information in Table 1 may be provided as part of an output for display on a monitor, a print out or as part of an ongoing evaluation of a patient's progress.

TABLE 1

| TREND INFO | last hour | last 24 hrs | last 7 days |
|---|---|---|---|
| Spontaneous Respiratory Rate (BPM) | 18 | 16 | 16 |
| Depth of Breathing (% of maximum) | 57 | 63 | 60 |
| Activity Level (% of maximum) | 77 | 75 | 80 |
| Coughing (per hour) | 20 | 20 | 20 |
| Mild Exacerbation (during period) | 0 | 3 | 3 |
| Moderate Exacerbation (during period) | 1 | 1 | 1 |
| Severe Exacerbation (during period) | 0 | 0 | 0 |
| Average Therapy Duration (min) | 35 | 70 | 75 |
| Volume Setting (ml) | 120 | 125 | 125 |

In addition or alternatively, the information in Table 1 can be displayed on the user interface of the ventilator, can be transmitted to a central monitoring station like a respiratory therapy department or nurse's station, or to a remote viewing or archiving location like a doctor's office, or can be formatted for printing and hard copy archival.

Additionally or alternatively, when a particular parameter from Table 1 is selected, for example, "Spontaneous Respiratory Rate", additional information can be viewed or expanded, as shown in the example Table 2 below, so that the therapeutic value can be compared with the baseline value.

TABLE 2

| Spontaneous Respiratory Rate (BPM) | BaseLine | With Therapy | % improved |
|---|---|---|---|
| Average | 22 | 18 | 18% |
| Minimum | 15 | 12 | |
| Maximum | 30 | 22 | |
| For Last: | 7 days | | |
| No. of Therapeutic Sessions: | 24 | | |
| Total Hours of Therapy: | 14 | | |

Additional details of ventilation systems and methods for providing ventilation therapy are described in International Application Number PCT/US2006/036600 and United States Patent Publication No. US2008/0135044.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:
1. A ventilator system comprising:
   a ventilator comprising a ventilation gas source, a ventilation gas delivery circuit, and a control unit;
   a patient interface in communication with the ventilation gas delivery circuit;
   at least one breath sensor;
   at least one patient activity sensor;

wherein the ventilator is adapted to be coupled to a patient for permitting ambulation of the patient while performing a portion of work for respiratory muscles of the patient by providing ventilation gas delivery, the ventilator capable of providing the ventilation gas delivery at an instantaneous flow rate of over 30 liters per minute; and wherein the control unit predicts a chronic obstructive pulmonary disease exacerbation based upon measurements from the at least one breath sensor and the at least one patient activity sensor and adjusts the ventilation gas delivery based upon the prediction to avoid or alleviate the chronic obstructive pulmonary disease exacerbation, wherein the control unit comprises a processor and a memory, and wherein the memory stores measured ventilation parameters regarding activity level of the patient, and wherein after a chronic obstructive pulmonary disease exacerbation, the measured ventilation parameters stored in the memory prior to the chronic obstructive pulmonary disease exacerbation are used to program a signature for predicting future chronic obstructive pulmonary disease exacerbations.

2. The ventilator system of claim 1, wherein the ventilator reports activity level to a remote device.

3. The ventilator system of claim 1, wherein the patient interface maintains an open airway system to permit the patient to breathe ambient air freely and spontaneously.

4. The ventilator system of claim 1, wherein the at least one patient activity sensor includes a pedometer to record ambulation of the patient.

5. The ventilator system of claim 1, wherein the at least one patient activity sensor includes an actigraphy sensor to record activity level of the patient.

6. The ventilator system of claim 1, wherein the control unit executes a patient exercise test mode.

7. The ventilator system of claim 1, wherein the control unit detects respiration from the at least one breath sensor and patient activity measure from the at least one patient activity sensor over a predetermined time and processes the respiration and the patient activity measure to adjust the ventilation.

8. The ventilator system of claim 7, wherein the respiration is a measure of consecutive breaths over the predetermined time, and ventilation is adjusted after a predetermined number of breaths at a predetermined rate.

9. The ventilator system of claim 8, wherein the control unit records trends from the at least one breath sensor and the at least one patient activity sensor.

10. The ventilation system of claim 9, wherein the trends indicate an onset or precursor to a chronic obstructive pulmonary disease exacerbation, and the control unit predicts the chronic obstructive pulmonary disease exacerbation based upon the trends.

11. The ventilator system of claim 10, wherein the control unit exports the trends indicating an onset or precursor to a chronic obstructive pulmonary disease exacerbation to an external source.

12. The ventilator system of claim 1, wherein the at least one breath sensor measures respiration information selected from the group consisting of: spontaneous breath rate, spontaneous breathing I:E ratio, spontaneous inspiratory and expiratory time, spontaneous depth of breathing, and combinations thereof.

13. The ventilator system of claim 1, further comprising a user interface for inputting health status normal values or health status goals, and wherein the user interface displays patient health status compared to the at least one health status normal values or health status goals.

14. The ventilator system of claim 1, wherein the at least one breath sensor measures respiration rate and the at least one patient activity sensor measures patient activity, and a combination of measurements by the at least one breath sensor and the at least one patient activity sensor is used to adjust the ventilation.

15. The ventilator system of claim 1, wherein the control unit adjusts the ventilation gas delivery further based upon at least one overall health goal.

16. The ventilator system of claim 15, wherein the at least one overall health goal includes increased patient well-being expressed on a well-being scale.

17. The ventilator system of claim 16, wherein the well-being scale is selected from the group consisting of Borg scale, comfort scale, dyspnea scale, tiredness scale, ease of breathing scale, quality of life scale, and combinations thereof.

18. The ventilator system of claim 1, wherein the ventilator introduces a medication other than oxygen through the ventilation gas delivery circuit in response to the prediction.

19. The ventilator system of claim 1, wherein the ventilator predicts the chronic obstructive pulmonary disease exacerbation based upon one or more factors selected from the group consisting of coughing, type of cough, mucus production level, breath rate, activity level, $SpO_2$, $EtCO_2$, and depth of breathing.

20. A ventilator system comprising:
a ventilator comprising a ventilation gas source, a ventilation gas delivery circuit, and a control unit;
a patient interface in communication with the ventilation gas delivery circuit;
at least one breath sensor;
at least one health status measuring sensor;
wherein the ventilator is adapted to be coupled to a patient for permitting ambulation of a patient while performing a portion of work for respiratory muscles of the patient by providing ventilation gas delivery, the ventilator capable of providing the ventilation gas delivery at an instantaneous flow rate of over 30 liters per minute; and
wherein the control unit predicts a chronic obstructive pulmonary disease exacerbation based upon measurements from the at least one breath sensor and the at least one health status measuring sensor and adjusts the ventilation gas delivery based upon the prediction to avoid or alleviate the chronic obstructive pulmonary disease exacerbation,
wherein the control unit comprises a processor and a memory, and wherein the memory stores measured ventilation parameters regarding the patient health status, and wherein after a chronic obstructive pulmonary disease exacerbation, the measured ventilation parameters stored in the memory prior to the chronic obstructive pulmonary disease exacerbation are used to program a signature for predicting future chronic obstructive pulmonary disease exacerbations.

21. The ventilator system of claim 20, wherein the ventilator reports patient health status to a remote device.

22. The ventilator system of claim 20, wherein the patient interface maintains an open airway system to permit the patient to breathe ambient air freely and spontaneously.

23. The ventilator system of claim 20, wherein the control unit executes a patient exercise test mode.

24. The ventilator system of claim 20, wherein the control unit detects respiration from the at least one breath sensor and patient health status from the at least one health status measuring sensor over a predetermined time and processes the respiration and the patient health status to adjust the ventilation.

25. The ventilator system of claim 24, wherein the respiration is a measure of consecutive breaths over the predetermined time, and ventilation is adjusted after a predetermined number of breaths at a predetermined rate.

26. The ventilator system of claim 20, wherein the at least one breath sensor measures respiration information selected from the group consisting of: spontaneous breath rate, spontaneous breathing I:E ratio, spontaneous inspiratory and expiratory time, spontaneous depth of breathing, and combinations thereof.

27. The ventilator system of claim 20, wherein the control unit records trends from the at least one breath sensor and the at least one health status measuring sensor.

28. The ventilator system of claim 27, wherein the trends indicate an onset or precursor to a chronic obstructive pulmonary disease exacerbation, and the control unit predicts the chronic obstructive pulmonary disease exacerbation based on the trends.

29. The ventilator system of claim 28, wherein the control unit exports the trends indicating an onset or precursor to a chronic obstructive pulmonary disease exacerbation to an external source.

30. The ventilator system of claim 20, wherein the control unit adjusts the ventilator to result in the health status that matches as close as possible to the health status baseline value.

31. The ventilator system of claim 20, wherein the at least one breath sensor measures respiration rate and the at least one health status measuring sensor measures the patient health status, and a combination of measurements by the at least one breath sensor and the at least one health status measuring sensor is used to adjust the ventilation.

32. The ventilator system of claim 20, wherein the ventilator introduces a medication other than oxygen through the ventilation gas delivery circuit in response to the prediction.

33. The ventilator system of claim 20, wherein the ventilator predicts the chronic obstructive pulmonary disease exacerbation based upon one or more factors selected from the group consisting of coughing, type of cough, mucus production level, breath rate, activity level, $SpO_2$, $EtCO_2$, and depth of breathing.

* * * * *